United States Patent
Shultz et al.

(10) Patent No.: US 7,090,975 B2
(45) Date of Patent: Aug. 15, 2006

(54) PYROPHOSPHOROLYSIS AND INCORPORATION OF NUCLEOTIDE METHOD FOR NUCLEIC ACID DETECTION

(75) Inventors: John W. Shultz, Verona, WI (US); Ryan J. Olson, Madison, WI (US); Christine Andrews, Cottage Grove, WI (US)

(73) Assignee: Promega Corporation, Madison, WI (US)

( * ) Notice: Subject to any disclaimer, the term of this patent is extended or adjusted under 35 U.S.C. 154(b) by 703 days.

(21) Appl. No.: 09/924,981

(22) Filed: Aug. 7, 2001

(65) Prior Publication Data

US 2003/0049624 A1 Mar. 13, 2003

Related U.S. Application Data

(63) Continuation-in-part of application No. 09/788,847, filed on Dec. 20, 2001, which is a continuation-in-part of application No. 09/406,064, filed on Sep. 27, 1999, now Pat. No. 6,270,973, which is a continuation-in-part of application No. 09/358,972, filed on Jul. 21, 1999, now Pat. No. 6,235,480, which is a continuation-in-part of application No. 09/252,436, filed on Feb. 18, 1999, now Pat. No. 6,159,693, which is a continuation-in-part of application No. 09/042,287, filed on Mar. 13, 1998, now Pat. No. 6,335,162.

(51) Int. Cl.
*C12Q 1/68* (2006.01)
*G01N 33/53* (2006.01)
*G01N 24/00* (2006.01)
*C12P 19/34* (2006.01)
*C07H 19/04* (2006.01)

(52) U.S. Cl. ............... 435/6; 435/7; 435/91.2; 435/91.5; 436/173; 436/501; 536/26; 536/27; 536/28; 935/77; 935/82

(58) Field of Classification Search ............... 435/6, 435/7, 91.2, 91.5; 436/173, 501; 536/26, 536/27, 28; 935/77, 82
See application file for complete search history.

(56) References Cited

U.S. PATENT DOCUMENTS

| | | | |
|---|---|---|---|
| 4,246,340 A | 1/1981 | Lundin et al. | 435/8 |
| 4,303,752 A | 12/1981 | Kolehmainen et al. | 435/8 |
| 4,331,762 A | 5/1982 | Nakajima et al. | 435/190 |
| 4,338,395 A | 7/1982 | Leon et al. | 435/17 |
| 4,352,881 A | 10/1982 | Inagawa et al. | 435/17 |
| 4,357,420 A | 11/1982 | Bostick et al. | 435/8 |
| 4,368,261 A | 1/1983 | Klose et al. | 435/15 |
| 4,371,611 A | 2/1983 | Fusee | 435/14 |
| 4,394,445 A | 7/1983 | Nix et al. | 435/19 |
| 4,415,655 A | 11/1983 | De Castro et al. | 435/17 |
| 4,438,124 A | 3/1984 | Meister et al. | 424/270 |
| 4,443,594 A | 4/1984 | Buckmann | 536/27 |
| 4,446,231 A * | 5/1984 | Self | 435/7 |
| 4,460,684 A * | 7/1984 | Bauer | 435/14 |
| 4,485,177 A | 11/1984 | Siedel et al. | 436/547 |
| 4,595,655 A * | 6/1986 | Self | 435/7 |
| 4,683,195 A | 7/1987 | Mullis et al. | 435/6 |
| 4,683,202 A | 7/1987 | Mullis et al. | 435/91 |
| 4,735,897 A * | 4/1988 | Vary et al. | 435/17 |
| 4,743,561 A * | 5/1988 | Shaffar | 436/501 |
| 4,755,458 A * | 7/1988 | Rabbani et al. | 435/5 |
| 4,800,159 A | 1/1989 | Mullis et al. | 435/172.3 |
| 5,229,285 A | 7/1993 | Kajiyama et al. | 435/6 |
| 5,356,776 A | 10/1994 | Kambara et al. | 435/6 |
| 5,389,512 A | 2/1995 | Sninsky | 435/5 |
| 5,391,480 A | 2/1995 | Davis et al. | 435/6 |
| 5,399,491 A * | 3/1995 | Kacian et al. | 435/6 |
| 5,401,837 A * | 3/1995 | Nelson | 536/25.32 |
| 5,403,711 A | 4/1995 | Walder et al. | 435/6 |
| 5,445,933 A * | 8/1995 | Eadie et al. | 435/6 |
| 5,491,133 A | 2/1996 | Walder et al. | 514/44 |
| 5,494,810 A | 2/1996 | Barany et al. | 435/91.52 |
| 5,498,523 A * | 3/1996 | Tabor et al. | 435/6 |
| 5,512,439 A | 4/1996 | Hornes et al. | 435/6 |

(Continued)

FOREIGN PATENT DOCUMENTS

| | | |
|---|---|---|
| EP | 0 229 601 A | 11/1986 |
| EP | 639 647 A | 7/1994 |
| EP | 0 663 447 A | 12/1994 |
| EP | 0 894 867 A | 11/1997 |
| GB | 22055200 | 12/1981 |
| WO | WO 90/05530 | 5/1990 |
| WO | WO 91/17264 | 11/1991 |
| WO | WO 92/13963 | 8/1992 |
| WO | WO 94/25619 | 11/1994 |
| WO | WO 95/21938 | 8/1995 |
| WO | WO 96/41014 | 12/1995 |
| WO | WO 97/41256 | 11/1997 |
| WO | WO 98/13523 | 4/1998 |
| WO | WO 98/54362 | 4/1998 |
| WO | WO 98/28440 | 7/1998 |
| WO | WO 98/54362 | 12/1998 |
| WO | WO 99/46409 | 9/1999 |
| WO | WO 00/49179 | 8/2000 |
| WO | WO 00/49180 | 8/2000 |
| WO | WO 00/49181 | 8/2000 |
| WO | WO 00/49182 | 8/2000 |

OTHER PUBLICATIONS

A.E. Sippel, "Purification and Characterization of Adenosine Triphosphate: Ribonucleic Acid Adenyltransferase from *Escherichia coli*" *Eur. J. Biochem.* 37:31–40 (1973).

(Continued)

*Primary Examiner*—Gary Benzion
*Assistant Examiner*—Arun Kvo Chakrabarti
(74) *Attorney, Agent, or Firm*—Welsh & Katz, Ltd.

(57) ABSTRACT

Processes are disclosed using the depolymerization of a nucleic acid hybrid and incorporation of a suitable nucleotide to qualitatively and quantitatively analyze for the presence of predetermined nucleic acid target sequences. Applications of those processes include the detection of single nucleotide polymorphisms, identification of single base changes, genotyping, medical marker diagnostics, mirosequencing, and.

28 Claims, No Drawings

U.S. PATENT DOCUMENTS

| | | | | | |
|---|---|---|---|---|---|
| 5,516,663 | A | * | 5/1996 | Backman et al. | 435/91.2 |
| 5,530,192 | A | | 6/1996 | Murase et al. | 800/205 |
| 5,541,311 | A | | 7/1996 | Dahlberg et al. | 536/23.7 |
| 5,561,044 | A | * | 10/1996 | Walker et al. | 435/6 |
| 5,573,906 | A | * | 11/1996 | Bannwarth et al. | 435/6 |
| 5,579,820 | A | | 12/1996 | Hornes et al. | 435/91.1 |
| 5,582,989 | A | | 12/1996 | Caskey et al. | 435/189 |
| 5,622,824 | A | | 4/1997 | Koster | 435/6 |
| 5,648,232 | A | * | 7/1997 | Squirrell | 435/34 |
| 5,660,988 | A | | 8/1997 | Duck et al. | 435/6 |
| 5,667,964 | A | | 9/1997 | Ho | 435/5 |
| 5,683,877 | A | | 11/1997 | Lu-Chang et al. | 435/6 |
| 5,691,146 | A | | 11/1997 | Mayrand | 435/6 |
| 5,723,591 | A | | 3/1998 | Livak et al. | 536/22.1 |
| 5,731,146 | A | | 3/1998 | Duck et al. | 435/6 |
| 5,736,365 | A | * | 4/1998 | Walker et al. | 435/91.2 |
| 5,741,635 | A | | 4/1998 | Boss et al. | 435/4 |
| 5,763,181 | A | | 6/1998 | Han et al. | 435/6 |
| 5,766,849 | A | * | 6/1998 | McDonough et al. | 435/6 |
| 5,786,139 | A | | 7/1998 | Burke et al. | 435/6 |
| 5,786,183 | A | * | 7/1998 | Ryder et al. | 435/91.2 |
| 5,814,491 | A | * | 9/1998 | Vijg et al. | 435/91.2 |
| 5,824,517 | A | | 10/1998 | Cleuziat et al. | 435/91.2 |
| 5,834,202 | A | * | 11/1998 | Auerbach | 435/6 |
| 5,840,873 | A | * | 11/1998 | Nelson et al. | 536/24.3 |
| 5,843,660 | A | | 12/1998 | Schumm et al. | |
| 5,849,547 | A | * | 12/1998 | Cleuziat et al. | 435/91.21 |
| 5,853,981 | A | | 12/1998 | Kondo et al. | 435/5 |
| 5,854,033 | A | * | 12/1998 | Lizardi | 435/91.2 |
| 5,861,242 | A | | 1/1999 | Chee et al. | 435/5 |
| 5,863,736 | A | | 1/1999 | Haaland | 435/6 |
| 5,866,337 | A | * | 2/1999 | Schon | 435/6 |
| 5,869,252 | A | * | 2/1999 | Bouma et al. | 435/6 |
| 5,871,902 | A | | 2/1999 | Weininger et al. | 435/5 |
| 5,876,924 | A | * | 3/1999 | Zhang et al. | 435/5 |
| 5,876,930 | A | | 3/1999 | Livak et al. | 435/6 |
| 5,876,978 | A | * | 3/1999 | Willey et al. | 435/91.2 |
| 5,880,473 | A | | 3/1999 | Ginestet | 250/458.1 |
| 5,882,856 | A | * | 3/1999 | Shuber | 435/6 |
| 5,885,775 | A | * | 3/1999 | Haff et al. | 435/6 |
| 5,888,819 | A | * | 3/1999 | Goelet et al. | 435/5 |
| 5,902,722 | A | | 5/1999 | Di Cesare et al. | 435/4 |
| 6,007,987 | A | | 12/1999 | Cantor et al. | 435/6 |
| 6,066,483 | A | | 5/2000 | Riggs et al. | 435/194 |
| 6,194,556 | B1 | * | 2/2001 | Acton | 536/23.2 |
| 6,235,480 | B1 | * | 5/2001 | Shultz | 435/6 |

OTHER PUBLICATIONS

K. Chowdhury, N. Kaushik, V.N. Pandey and M.J. Modak, "Elucidiation of the Role of Arg 110 of Murine Leukemia Virus Reverse Transcriptase in the Catalytic Mechanism: Biochemical Characterization of Its Mutant Enzymes," *Biochemisty*, 35:16610–16620 (1996).

S. Karamohamed, M. Ronaghi and P. Nyren, "Bioluminometric Method for Real–Time Detection of Reverse Transcriptase Activity", *Biotechniques*, 24:302–306 (Feb., 1998).

B. Hove–Jensen, K.W. Harlow, C.J. King, R.L. Switzer, "Phosphoribosylpyrophosphate Syntetase of *Escherichia coli*", *J. Biol. Chem.*, 261(15):6765–6771 (1986).

P. Nyren, S. Karamohamed and M. Ronaghi, "Detection of Single–Base Changes Using a Bioluminometric Primer Extension Assay", *Anal. Biochem.*, 244:367–373 (Jan. 15, 1997).

M. Ronaghi, S. Karamohamed, B. Pettersson, M. Uhlen and P. Nyren, "Real–Time DNA Sequencing Using Detection of Pyrophosphgate Release," *Anal. Biochem.*, 242:84–89 (1996).

T.A. Rozovskaya, V.O. Rechinsky, R.S. Bibilashvili, M.Y. Karpeisky, N.B. Tarusova, R.M. Khomutov, H.B.F. Dixon, "The Mechanism of Pyrophosphorolysis of RNA by RNA Polymerase", *Biochem. J.*, 224:645–650 (1989).

M.P. Deutscher and A. Kornberg, "Enzymatic Synthesis of Deoxyribonucleic Acid", *J. Biol. Chem.*, 244(11):3019–28 (1969).

J.D. Moyer and J.F. Henderson, "Nucleoside Triphosphate Specificity of Firefly Luciferase", *Anal. Biochem.*, 131:187–189 (1983).

C. Blondin, L. Serina, L. Weismuller, A. Gilles and O. Barzu, "Improved Spectrophotometric Assay of Nucleoside Monophosphate Kinase Activity Using the Pyruvate Kinase/Lactate Dehydrogenase Coupling System", *Anal. Biochem.*, 220:219–21 (1994).

Tabor and C.C. Richardson, "DNA Sequence Analysis With a Modified Bacteriophage T7 DNA Polymerase", *J. Biol. Chem.*, 265(14):8322–8328 (1990).

R.S. Chittock, J.–M. Hawronsky, J. Holah and C.W. Wharton, "Kinetic Aspects of ATP Amplification Reactions", *Anal. Biochem.*, 255:120–126 (Jan. 1, 1998).

Kung, et al., "Picogram Quantitation of Total DNA Using DNA–Binding Proteins in a Silicon Sensor–Based System", *Anal. Biochem.*, 187:220–227 (1990).

Srivastavan & Modak, "Enzymatic Activities Associated With Avian and Murine Retroviral DNA Polymerases," *J. Biol. Chem.*, 255(5):2000–2004 (1980).

Sano & Feix, "Terminal Riboadenylate Transferase from *Escherichia coli*" (Characterization and Application) *Eur. J. Biochem.*, 71:577–583 (1976).

Sabina, et al., "The Enzymatic Synthesis of 5–Amino–4 Imidazolecarboxamide Riboside Triphhosphate (ZTP)," *Science*, 223:1193–1195 (1984).

Parks & Agarwal in *The Enzymes*, "Nucleoside Diphosphokinases," vol. 9:307–333, P. Boyer Ed. (1973).

Shimofuruya & Suzuki, "Pyrimidine Nucleoside Monophosphate Kinase Isolated From Pig Brain Homogenate Catalyzes Disproportionation of Phosphate Between Two CD Molecules," *Biochem. Intl.*, 26(5):853–861 (1992).

Nyren, et al., "Detection of Single–Base Changes Using a Bioluminometric Primer Extension Assay", *Anal. Biochem.*, 244:267–373 (1997).

P. Bernard et al., "Homogeneous Multiplex Genotyping of Hemochromatosis Mutations With Fluorescent Hybridization Probes," *American Journal of Pathology*, 153(4) 1055–1061.

G. Garinis et al., *J. Clin. Lab. Anal.*, 13:122–125 (1999).

Holguin, et al., "Comparison of Three Different Commercial Methods for Measuring Plasma Viraemia in Patients Infected With Non–B HIV–1 Subtypes," *Eur. J. Clin. Microbiol. Infect. Dis.* 18:256–259 (1999).

Boriskin, et al., "Viral Loads In Dual Infection With HIV–1 and Cytomegalovirus," *Arch. Dis. Child.*, 80:132–136 (1999).

De Vega, et al., "Primer Terminus Stabilizing at the 3'–5' Exonuclease Active site of Ø29 DNA Polymerase. Involvement of two amino acid residues highly conserved in proofreading DNA polymerases", *EMBO J.*, 15(5):1182–1192 (1996).

S. Patel et al., "Pre–Steady–State Kinetic Analysis of Processive DNA Replication Including Complete Characterization of an Exonuclease–Deficient Mutant," *Biochemistry*, 30:511–525 (1991).

I. Wong et al., "An Induced–Fit Kinetic Mechanism for DNA Replication Fidelity: Direct Measurement by Single–Turnover Kinetics," *Biochemisty*, 30:526–537 (1991).

S. Zinnen et al., "Misincorporation and Mispaired Primer Extension by Human Immunodeficiency Virus Reverse Transcriptase," *J. Biological Chemistry*, 269(39):24195–24202 (1994).

J. Lindquist, "Dilution Theory—p. 3—The Most–Probable Number (MPN) Method," Dept. of Bacteriology, University of Wisconsin–Madison,http://www.bact.wisc.edu/bact102/102dil3.html.

J. Lindquist, "Dilutin Theory—Supplement to p. 3—The Most–Probable Numbe (MPN) Method: A Five–Tube MPN Table," Dept. of Bacteriology, University of Wisconsin–Madison, http://www.bact.wisc.edu/bact102/102dil3a.html.

"Most Probable Number (MPN)," WQA Glossary of Terms, 3rd Ed., Water Quality Association.

P. Nyren, B. Pettersson, and M. Uhlen., "Solid Phase DNA Minisequencing by an Enzymatic Luminometric Inorganic Pyrophosphate Detection Assay," *Anal. Biochem.*, 208:171–175 (1993).

M. Ronaghi, S. Karamohamed, B. Pettersson, M. Uhlen, and P. Nyren, "Real–Time DNA Sequencing Using Detection of Pyrophosphate Release," *Anal. Biochem.*, 242:84–89 (1996).

J. Shultz, D. Leippe, K. Lewis, R. Lyke, M. Nelson, and C. Reynolds., "Detection of Low Levels of Nucleic Acids by Enzymatic Conversion to Substrates for Luciferase", Poster presented at a Protein Society meeting in San Diego, California.

Heid, et al., "Real Time Quantitative PCR", *Genome Research*, 6:986–994 (1996).

Nagano, et al., "Detection of Verotoxin–Producing *Escherchia coli* O157:H7 by Multiplex Polymerase Chain Reaction", *Microbiol. Immunol.*, 42(5), 372–376 (1998).

Sherlock, et al., "Assessment of diagnostic quantitative fluorescent multiplex polymerase chain reaction assays performed on single cells", *Ann. Hum. Genet.* 62:9–23 (1998).

Axton, et al., "A Single–Tube Multiplex System for the Simultaneous Detection of 10Common Cystic Fibrosis Mutations", *Human Mutation*, 5:260–262 (1995).

Poyser et al., "Multiplex genotyping for cystic fibrosis from filter paper blood spots", *Ann. Clin. Biochem.*, 35:611–615 (1998).

Caeudai, et al., "Detection of HCV and GBV–C/HGV injection by multiplex PCR in plasma samples of transfused subjects", *J. Virol Meth.*, 70: 79–83 (1998).

Songsivilai, et al., "Improved Amplification System for Detection of Hepatitis C virus Genome that Simultaneously Differentiates Viral Genotype", *Southeast Asian J. Trop. Med. Public Health*, 27(2): 237–243 (1996).

Oyofo, et al., "Detection of Enterotoxigenic *Escherichia coli*, Shigella and Campylobacter spp. by Multiplex PCR Assay", *J. Diarrhoeal Dis. Res.*, 14(3): 207–210 (1996).

L. Ripoll, et al., "Multiplex PCR–mediated Site–directed Mutagenesis for One–step Determination of Factor V Leiden and G20210A Transition of the Prothrombin Gene", pp. 960–961 (1997).

L. Ripoll, et al., "Multiplex ASA PCR for a Simultaneous Determination of Factor V Leiden Gene, G—A 20210 Prothrombin Gene and C—T 677 MTHFR Gene Mutations", *Thromb Haemost*, 79:1054–1055 (1998).

X. Xu et al., "Two Multiplex PCR–Based DNA Assays for the Thrombosis Risk Factors Prothrombin G20210A and Coagulation Factor V G1691A Polymorphisms" *Thrombosis Research* 93:265–269 (1999).

E. Gomez, et al., "Rapid Simultaneous Screening of Factor V Leiden and G20210A Prothrombin Variant by Multiplex Polymerase Chain Reaction on Whole Blood", *Blood* 91(6):2208–2211 (1998).

D. Linfert, et al., "Rapid Multiplex Analysis for the Factor V Leiden and Prothrombin G20210A Mutations Associated with Hereditary Thrombophilia", *Connecticut Medicine* 62(9):519–525 (1998).

P. Nyren, et al., "Detecton of Single–Base Changes Using A Bioluminometric Primer Extension Assay," *Anal. Biochem.*, 244:367–373 (1997).

S. Borman, "Developers of Novel DNA Sequencers Claim Major Performance Advances", *C&EN*, pp. 37–40 (1995).

P. Belgrader, et al., "PCR Detection of Bacteria in Seven Minutes", *Science Magazine* 284:449–450 (1999).

K. Hayashi, "PCR–SSCP: A Method for Detection of Mutations," *Geneteic Analysis: Techniques and Applications* 9:73–79 (1992).

Newton et al., "Analysis of Any Point Mutation in DNA, The Amplificaton Refractory Mutation System (ARMS)," *Nucl. Acids Res.*, 17:2503–2516 (1989).

Wu et al., "Allele–Specific Enzymatic Amplification of β–Globin Genomic DNA for Diagnosis of Sickle Cell Anemia,"*Proc. Natl. Acad. Sci., USA*, 86:2757–2760 (1989).

T. Nikiforov, et al., "Genetic Bit Analysis: A Solid Phase Method for Typing Single Nucleotide Polymorphisms," *Nucl. Acids Res.*, 22:4167–4175 (1994).

C. Wittwer, et al., "Continuous Fluorescence Monitoring of Rapid Cycel DNA Amplification," *Biotechniques*, 22:130–138 (1997).

P. Holland, et al., "Detection of Specific Polymerase Chain Reaction Product by Utilizing the 5'→3' Exonuclease Activity of *Thermus Aquaticus* DNA Polymerase," *Proc. Natl. Acad. Sci., USA*, 88:7276–7280 (1991).

R. Kramer, et al., "Molecular Beacons: Probes that Fluorescfe Upon Hybridizaiton," *Nat. Biotechnol.*, 14:303–308 (1996).

J. Shultz, D. Leippe, K. Lewis and M. Nelson, "Non–radioactive Measurement of DNA Using Coupled Enzymatic Reactions", Presentation Mar. 16–20, 1998 at a Parental Drug Association meeting in San Francisco, California.

Seq ID No.1, "Blast Archaeal Genome Sequences at Center of Marine Biotechnology" Online, May 21, 1999, Retrieved on 8/7/200 @ http://Combdna.umbi.umd.edu/hags.html.

http://Comb5–156.umbi.umd.edu/cgi–bin/PfurGene. PL?GeneID=894645&Dataset=Nayb&Geneidtxt–994645, Online! XP002144446, Retrieved from the internet on Aug. 7, 2000.

Giartosio, et al., "Thermal stability of hexameric and tetrameric nucleoside diphosphate kinases: Effect of subunit interaction", *J. Biol. Chem.*, 271(30):17845–17851 (1996).

Bi, W., et al., "Detection of known mutation by proof–reading PCR", *Nucleic Acid Research*, GB, 26(12):3073–3075 (1998).

Kawarabayashi, et al., "Complete Sequence and Gene Organization of the Genome of hyper–thermophilic Archaebacterium, *Pyrococcus horikoshii* OT3", *DNA Research*, 5:55–76 (1998).

Carl W. Schmid, "Alu: Structure, Origin, Evolution, Significance, and Function of One–Tenth of Human DNA," *Prog. in Nucl. Acid Res. and Mol. Biol.*, 53:283–319 (1996).

Hamdi, et al., "Origin and Phylogenitic Distribution of *Alu* DNA Repeats: Irreversible Events in the Evolution of Primates," *J. Mol. Biol.* (1999).

P.L. Deininger and M.A. Batzer, "*Alu* Repeats and Human Disease", Mol. Genet. Metab., 67 (3): 183–193 (1999).

Batzer, et al., "Standardized Nomenclature for *Alu* Repeats," *J. Mol. Evol.*, 42:3–6 (1996).

P. Deininger, et al., "Master Genes in Mammalian Repetitive DNA Amplification," *Trend Genet.*, 8:307 (1992).

T. D. Kocher, et al., "Dynamics of Mitochondrial DNA Evolution in Animals: Amplification and Sequencing with Conserved Primers," *Proc. Nat.'l Acad. Sci.*, U.S.A., 86:6196–6200.

Mizrahi, et al., "Mechanisms of DNA polymerase I: Exonuclease/polymerase activity switch and DNA sequence dependence of pyrophosphorolysis and misincorporation reactions," *Proc. Natl. Acad. Sci., USA* 83:5769–5773 (Aug. 1986).

Weichenrieder, et al., "*Structure and Assembly of the Alu Domain of the Mammalian Signal Recognition Particle*," Nature, 408(9): 167–173 (Nov., 2000).

J. Gregor Sutcliffe, et al., "*Commun 82–Nucleotide Sequence Unique to Brain RNA*," Pract. Nat. Acad. Sci., U.S.A., 79:4942–4946 (Aug., 1982).

Van Essen et al., *J. Med. Genet.*, 34:805–12 (1997).

Calvano et al., *Clin. Genet.* 52:17–22 (1997).

Jongpiputvanich et al., *J. Med. Assoc. Thai.* 79(Supp. 1):S15–21 (1996).

Pastore et al., *Mol. Cell. Probes* 10:129–37 (1996).

Katayama et al., *Fetal Diagn. Ther.* 9:379–84 (1994).

Shohet et al., *Arterioscler. Thromb. Vasc. Biol.* 19:1975–78 (1999).

Boerma et al., *Intern. Med.*, 246:211–218 (1999).

Sugiyama et al., *Mutat.* 14:90 (1999).

Wei et al., *Nature*, 399:243(1999).

Niessen W., *J. Chromatog. A* 794:407–435 (1998).

Jain, et al., *Biochem. Biophys. Res. Commun.*, 200:1239–1244 (1994).

Levitt, B. et al., *Anal. Biochem.* 137:93–100(1984).

Revich et al., *J. Chromatography*, 317:283–300 (1984).

Perrone & Brown, *J. Chromatography*, 317:301–310 (1984).

\* cited by examiner

PYROPHOSPHOROLYSIS AND INCORPORATION OF NUCLEOTIDE METHOD FOR NUCLEIC ACID DETECTION

CROSS-REFERENCE TO RELATED APPLICATIONS

This application is a continuation-in-part of allowed U.S Ser. No. 09/788,847, filed Feb. 20, 2001 which is a division of U.S. Ser. No. 09/406,064 filed Sep. 27, 1999 now U.S. Pat. No. 6,270,973, issued Aug. 7, 2001, which is a continuation-in-part of U.S. Ser. No. 09/358,972, filed on Jul. 21, 1999, now U.S. Pat. No. 6,235,480 issued May 22, 2001, which is a continuation-in-part of U.S. Ser. No. 09/252,436, filed on Feb. 18, 1999, now U.S. Pat. No. 6,159,693, issued Dec. 12, 2000, which is a continuation-in-part of allowed U.S. Ser. No. 09/042,287, filed Mar. 13, 1998, all of which are incorporated herein by reference.

TECHNICAL FIELD

The invention relates to nucleic acid detection. More specifically, the invention relates to the determination of the presence or absence of targeted, predetermined nucleic acid sequences in nucleic acid target/probe hybrids, and the various applications of their detection.

BACKGROUND OF THE INVENTION

Methods to detect specific nucleic acids provide a foundation upon which the large and rapidly growing field of molecular biology is built. There is constant need for alternative methods and products. The reasons for selecting one method over another are varied, and include a desire to avoid radioactive materials, the lack of a license to use a technique, the cost or availability of reagents or equipment, the desire to minimize the time spent or the number of steps, the accuracy or sensitivity for a certain application, the ease of analysis, the need to detect multiple nucleic acids in one sample, or the ability to automate the process.

The detection of specific nucleic acids is often a portion of a process rather than an end in itself. There are many applications of the detection of nucleic acids in the art, and new applications are always being developed. The ability to detect and quantify nucleic acids is useful in detecting microorganisms, viruses and biological molecules, and thus affects many fields, including human and veterinary medicine, food processing and environmental testing. Additionally, the detection and/or quantification of specific biomolecules from biological samples (e.g. tissue, sputum, urine, blood, semen, saliva) has applications in forensic science, such as the identification and exclusion of criminal suspects and paternity testing as well as medical diagnostics.

Some general methods to detect nucleic acid hybrids are not dependent upon a priori knowledge of the nucleic acid sequence. Duplex DNA can be detected using intercalating dyes such as ethidium bromide. Such dyes are also used to detect hybrid formation.

Several hybridization methods to detect nucleic acids are dependent upon knowledge of the nucleic acid sequence. Many known nucleic acid detection techniques depend upon specific nucleic acid hybridization in which an oligonucleotide probe is hybridized or annealed to nucleic acid in the sample or on a blot, and the hybridized probes are detected.

A traditional type of process for the detection of hybridized nucleic acid uses labeled nucleic acid probes to hybridize to a nucleic acid sample. For example, in a Southern blot technique, a nucleic acid sample is separated in an agarose gel based on size and affixed to a membrane, denatured, and exposed to the labeled nucleic acid probe under hybridizing conditions. If the labeled nucleic acid probe forms a hybrid with the nucleic acid on the blot, the label is bound to the membrane. Probes used in Southern blots have been labeled with radioactivity, fluorescent dyes, digoxygenin, horseradish peroxidase, alkaline phosphatase and acridinium esters.

Another type of process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe. PCR-based methods are of limited use for the detection of nucleic acid of unknown sequence.

In a PCR method, the amplified nucleic acid product may be detected in a number of ways, e.g. incorporation of a labeled nucleotide into the amplified strand by using labeled primers. Primers used in PCR have been labeled with radioactivity, fluorescent dyes, digoxygenin, horseradish peroxidase, alkaline phosphatase, acridinium esters, biotin and jack bean urease. PCR products made with unlabeled primers may be detected in other ways, such as electrophoretic gel separation followed by dye-based visualization.

Multiplex PCR assays are well known in the art. For example, U.S. Pat. No. 5,582,989 discloses the simultaneous detection of multiple known DNA sequence deletions. The technique disclosed therein uses a first set of probes to hybridize to the targets. Those probes are extended if the targets are present. The extension products are amplified using PCR.

Fluorescence techniques are also known for the detection of nucleic acid hybrids, U.S. Pat. No. 5,691,146 describes the use of fluorescent hybridization probes that are fluorescence-quenched unless they are hybridized to the target nucleic acid sequence. U.S. Pat. No. 5,723,591 describes fluorescent hybridization probes that are fluorescence-quenched until hybridized to the target nucleic acid sequence, or until the probe is digested. Such techniques provide information about hybridization, and are of varying degrees of usefulness for the determination of single base variances in sequences. Some fluorescence techniques involve digestion of a nucleic acid hybrid in a 5'→3' direction to release a fluorescent chemical entity from proximity to a fluorescence quencher, for example, TaqMan® (Perkin Elmer; U.S. Pat. Nos. 5,691,146 and 5,876,930).

Enzymes having template-specific polymerase activity for which some 3'→5' depolymerization activity has been reported include *E. coli* DNA Polymerase (Deutscher and Kornberg, *J. Biol. Chem.*, 244(11):3019–28 (1969)), T7 DNA Polymerase (Wong et al., *Biochemistry* 30:526–37 (1991); Tabor and Richardson, *J. Biol. Chem.* 265: 8322–28 (1990)), *E. coli* RNA polymerase (Rozovskaya et al., *Biochem. J.* 224:645–50 (1994)), AMV and RLV reverse transcriptases (Srivastava and Modak, *J. Biol. Chem.* 255: 2000–4 (1980)), and HIV reverse transcriptase (Zinnen et al., *J. Biol. Chem.* 269:24195–202 (1994)). A template-dependent polymerase for which 3' to 5' exonuclease activity has been reported on a mismatched end of a DNA hybrid is phage 29 DNA polymerase (de Vega, M. et al. *EMBO J.*, 15:1182–1192, 1996).

A variety of methodologies currently exist for the detection of single nucleotide polymorphisms (SNPs) that are present in genomic DNA. SNPs are DNA point mutations or insertions/deletions that are present at measurable frequencies in the population. SNPs are the most common variations in the genome. SNPs occur at defined positions within genomes and can be used for gene mapping, defining population structure, and performing functional studies. SNPs are useful as markers because many known genetic diseases are caused by point mutations and insertions/deletions. Some SNPs are useful as markers of other disease genes because they are known to cosegregate.

In rare cases where an SNP alters a fortuitous restriction enzyme recognition sequence, differential sensitivity of the amplified DNA to cleavage can be used for SNP detection. This technique requires that an appropriate restriction enzyme site be present or introduced in the appropriate sequence context for differential recognition by the restriction endonuclease. After amplification, the products are cleaved by the appropriate restriction endonuclease and products are analyzed by gel electrophoresis and subsequent staining. The throughput of analysis by this technique is limited because samples require processing, gel analysis, and significant interpretation of data before SNPs can be accurately determined.

Single strand conformational polymorphism (SSCP) is a second technique that can detect SNPs present in an amplified DNA segment (Hayashi, K. *Genetic Analysis: Techniques and Applications* 9:73–79, 1992). In this method, the double stranded amplified product is denatured and then both strands are allowed to reanneal during electrophoresis in non-denaturing polyacrylamide gels. The separated strands assume a specific folded conformation based on intramolecular base pairing. The electrophoretic properties of each strand are dependent on the folded conformation. The presence of single nucleotide changes in the sequence can cause a detectable change in the conformation and electrophoretic migration of an amplified sample relative to wild type samples, allowing SNPs to be identified. In addition to the limited throughput possible by gel-based techniques, the design and interpretation of SSCP based experiments can be difficult. Multiplex analysis of several samples in the same SSCP reaction is extremely challenging. The sensitivity required in mutation detection and analysis has led most investigators to use radioactively labeled PCR products for this technique.

In the amplification refractory mutation system (ARMS, also known as allele-specific PCR or ASPCR), two amplification reactions are used to determine if a SNP is present in a DNA sample (Newton et al. *Nucl Acids Res* 17:2503, 1989; Wu et al. *PNAS* 86:2757, 1989). Both amplification reactions contain a common primer for the target of interest. The first reaction contains a second primer specific for the wild type product which will give rise to a PCR product if the wild type gene is present in the sample. The second PCR reaction contains a primer that has a single nucleotide change at or near the 3' end that represents the base change that is present in the mutated form of the DNA. The second primer, in conjunction with the common primer, will only function in PCR if genomic DNA that contains the mutated form of genomic DNA is present. This technique requires duplicate amplification reactions to be performed and analyzed by gel electrophoresis to ascertain if a mutated form of a gene is present. In addition, the data must be manually interpreted.

Single base extension (GBA®) is a technique that allows the detection of SNPs by hybridizing a single strand DNA probe to a captured DNA target (Nikiforov, T. et al. *Nucl Acids Res* 22:4167–4175). Once hybridized, the single strand probe is extended by a single base with labeled dideoxynucleotides. The labeled, extended products are then detected using calorimetric or fluorescent methodologies.

A variety of technologies related to real-time (or kinetic) PCR have been adapted to perform SNP detection. Many of these systems are platform based, and require specialized equipment, complicated primer design, and expensive supporting materials for SNP detection. In contrast, the process of this invention has been designed as a modular technology that can use a variety of instruments that are suited to the throughput needs of the end-user. In addition, the coupling of an automatable format with standard oligonucleotide chemistry and well-established enzymology provides a flexible and open system architecture. Alternative analytical detection methods, such as mass spectroscopy, HPLC, and fluorescence detection methods can also be used in the process of this invention, providing additional assay flexibility.

SNP detection using real-time amplification relies on the ability to detect amplified segments of nucleic acid as they are generated during the amplification reaction. Three basic real-time SNP detection methodologies exist: (i) increased fluorescence of double strand DNA specific dye binding, (ii) decreased quenching of fluorescence during amplification, and (iii) increased fluorescence energy transfer during amplification (Wittwer, C. et al. *Biotechniques* 22:130–138, 1997). All of these techniques are non-gel based and each strategy will be briefly discussed.

A variety of dyes are known to exhibit increased fluorescence in response to binding double stranded DNA. This property is utilized in conjunction with the amplification refractory mutation system described above to detect the presence of SNP. Production of wild type or mutation containing PCR products are continuously monitored by the increased fluorescence of dyes such as ethidium bromide or Syber Green as they bind to the accumulating PCR product. Note that dye binding is not selective for the sequence of the PCR product, and high non-specific background can give rise to false signals with this technique.

A second detection technology for real-time PCR, known generally as exonuclease primers (TaqMan® probes), utilizes the 5' exonuclease activity of thermostable polymerases such as Taq to cleave dual-labeled probes present in the amplification reaction (Wittwer, C. et al. *Biotechniques* 22:130–138, 1997; Holland, P et al *PNAS* 88:7276–7280, 1991). While complementary to the PCR product, the probes used in this assay are distinct from the PCR primer and are dually-labeled with both a molecule capable of fluorescence and a molecule capable of quenching fluorescence. When the probes are intact, intramolecular quenching of the fluorescent signal within the DNA probe leads to little signal. When the fluorescent molecule is liberated by the exonuclease activity of Taq during amplification, the quenching is greatly reduced leading to increased fluorescent signal.

An additional form of real-time PCR also capitalizes on the intramolecular quenching of a fluorescent molecule by use of a tethered quenching moiety. The molecular beacon technology utilizes hairpin-shaped molecules with an internally-quenched fluorophore whose fluorescence is restored by binding to a DNA target of interest (Kramer, R. et al. *Nat. Biotechnol.* 14:303–308, 1996). Increased binding of the molecular beacon probe to the accumulating PCR product can be used to specifically detect SNPs present in genomic DNA.

A final, general fluorescent detection strategy used for detection of SNP in real time utilizes synthetic DNA segments known as hybridization probes in conjunction with a process known as fluorescence resonance energy transfer (FRET) (Wittwer, C. et al. *Biotechniques* 22:130–138, 1997; Bernard, P. et al. *Am. J. Pathol.* 153:1055–1061, 1998). This technique relies on the independent binding of labeled DNA probes on the target sequence. The close approximation of the two probes on the target sequence increases resonance energy transfer from one probe to the other, leading to a unique fluorescence signal. Mismatches caused by SNPs that disrupt the binding of either of the probes can be used to detect mutant sequences present in a DNA sample.

There is a need for alternative methods for the detection of a plurality of nucleic acid hybrids in a single sample (multiplexing). There is a demand for such methods that are highly sensitive. For example methods to determine viral load of multiple viruses in a single sample that are able to reliably detect as few as 10 copies of a virus present in a body, tissue, fluid, or other biological sample would be in high demand. There is a great demand for methods to determine the presence or absence of nucleic acid sequences that differ slightly from sequences that might otherwise be present. There is a great demand for methods to determine the presence or absence of sequences unique to a particular species in a sample. There is also a great demand for methods that are more highly sensitive than the known methods, quantitative, highly reproducible and automatable.

It would be beneficial if another method were available for detecting the presence of a sought-after, predetermined target nucleotide sequence or allelic or polynucleotide variant. It would also be beneficial if such a method were operable using a sample size of the microgram to picogram scale. It would further be beneficial if the various methods listed above were capable of providing multiple analyses in a single assay (multiplex assays). The disclosure that follows provides a wide variety of methods and materials for nucleic acid hybrid detection.

SUMMARY OF THE INVENTION

The present invention contemplates methods and materials for determining the presence or absence of a nucleic acid hybrid. The convenient assays can use inexpensive reagents, such as unlabeled probes. The only enzyme necessary for most embodiments is a template-dependent polymerase. The assays are amenable to a very high degree of multiplexing and automation.

A sample that may contain a nucleic acid hybrid is maintained under conditions that permit pyrophosphorolysis. Analysis to determine whether or not pyrophosphorolysis occurs involves the addition of a nucleotide to a pyrophosphorylyzed 3'-terminal region in the nucleic acid hybrid. The pyrophosphorolysis followed by the incorporation of a nucleotide is the foundation of the present invention.

A contemplated reaction mixture for determining the presence or absence of a nucleic acid hybrid in a sample contains a sample that may have a nucleic acid hybrid, pyrophosphate, an enzyme that catalyzes pyrophosphorolysis of a 3'-terminal region of the nucleic acid hybrid, and a suitable nucleotide that can be incorporated into the 3'-terminal region in place of a pyrophosphorylyzed residue. The reaction mixture can include other components that do not materially affect the pyrophosphorolysis and nucleotide incorporation in the reaction mixture.

A contemplated method comprises the steps that follow. A reaction mixture as described above is provided and maintained for a time period and under conditions that permit pyrophosphorolysis of the 3'-terminus of a strand of the nucleic acid hybrid to form a modified 3'-terminal region and the incorporation of a suitable nucleotide onto the modified 3'-terminus. The reaction solution after maintaining the reactions is referred to as a "treated sample". The treated nucleic acid sample is provided that may contain a nucleic acid hybrid. Many preferred embodiments involve the purposeful generation of specific nucleic acid hybrid formation using nucleic acid probes that hybridize to predetermined nucleic acid targets.

The sample is maintained under conditions that permit pyrophosphorolysis in the presence of pyrophosphate and in the presence of an enzyme capable of catalyzing the release of a nucleotide from the 3'-terminus of one of the strands of the nucleic acid hybrid when pyrophosphate is present. The treated sample is assayed to determine whether pyrophosphorolysis of the nucleic acid hybrid occurs. If pyrophosphorolysis occurs, then an appropriate nucleic acid hybrid is present. Conversely, if there is no pyrophosphorolysis, then the nucleic acid hybrid is not present in the sample. In preferred embodiments, a nucleotide is incorporated into the pyrophosphorylyzed nucleic acid strand in a template-dependent manner.

In preferred embodiments, the same enzyme catalyzes both specific reactions. In preferred embodiments, the enzyme performing both reactions is a template-dependant polymerase. In some preferred embodiments, the enzyme is a thermostable template-dependent polymerase.

Determination of whether or not a nucleotide is incorporated into the pyrophosphorylyzed 3'-terminus is done using any method of analyzing nucleic acids. One contemplated class of analytical methods involves the incorporation of labels to determine whether nucleotide incorporation occurs. Many such methods involve separation of free nucleotides from nucleic acid polymers, including but not limited to gel separation methods. Another contemplated class of analytical methods do not rely upon the incorporation of labels, but involve a determination of relative sizes of a nucleic acid probe. These methods also include but are not limited to gel separation methods. Another contemplated class of analytical methods may involve incorporation of a capture tag such that only products of the invention are selected from the group of probes. Alternatively, the probe or the template itself may contain a capture tag and any known method of analyzing DNA is useful to assess the pyrophophorolysis/nucleotide incorporation step.

The present invention provides methods and materials useful for detecting nucleic acid hybrids in a variety of applications.

DETAILED DESCRIPTION OF THE INVENTION

The present disclosure provides methods and materials for the qualitative or quantitative determination of a nucleic acid hybrid. A contemplated detection method builds upon the pyrophosphorolysis methods of nucleic acid hybrid detection disclosed in the earlier patents that are cross-referenced above and incorporated in full herein by reference. Briefly, the invention contemplates the determination of whether a nucleic acid hybrid had been pyrophosphorylyzed to release nucleotides by the addition of a nucleotide to the pyrophosphorylyzed nucleic acid strand. Thus, a method embodiment of the invention comprises a depolymerization and incorporation of nucleotide (reincorporation).

The description that follows discusses in greater detail (A) the depolymerization and nucleotide incorporation reactions, (B) the substrates, (C) the enzyme, (D) the reaction conditions, (E) multiplex variations, (F) analytical output, (G) applications of the technology, and (H) kits.

A. Nucleic Acid Hybrid Detection Via Depolymerization and Incorporation of Nucleotide The parent cases disclose materials and methods for nucleic acid detection via depolymerization of a nucleic acid hybrid. One of the depolymerization reactions disclosed therein is pyrophosphorolysis. Several methods were disclosed therein for ascertaining whether or not depolymerization of the nucleic acid hybrid had occurred, and thereby for detection of the nucleic acid hybrid. The present invention is concerned with ascertaining whether or not depolymerization of a nucleic acid hybrid occurred via incorporation of nucleotide, preferably catalyzed by the same enzyme.

i. Depolymerization

The present invention involves methods and materials for the pyrophosphorolysis of the 3' end of a strand of a nucleic acid hybrid. An illustrative nucleic acid hybrid is shown below with a 5' overhang (though it also works at the 3' terminus of blunt-ended hybrids) where pyrophosphorolysis occurs in the presence of inorganic pyrophosphate and an enzyme that catalyzes pyrophosphorolysis, such as a template-dependent polymerase.

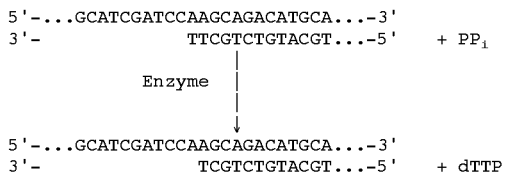

The pyrophosphorolysis reaction is separate and distinct from a "proofreading" reaction where an incorrectly incorporated nucleic acid base is excised from a growing nucleic acid chain. That "proofreading" function is associated with a separate and distinct 3' to 5' exonuclease activity. The proofreading function is so distinct from the polymerase reaction that in the Klenow fragment of *E. coli* DNA polymerase, it is possible to remove one enzyme activity without eliminating the other (e.g. "Klenow exo-minus"). Klenow exo-minus is capable of catalyzing both polymerization and pyrophosphorolysis.

The pyrophosphorolysis reaction is also different from an endonucleolytic cleavage, where a nucleic acid chain is cleaved, not at the end, but at an internal position. Typical endonucleolytic cleavages cleave both strands at a specific endonuclease recognition site.

ii. Incorporation of Nucleotide

The cross-referenced parent cases discuss various methods of detecting whether or not depolymerization (in this embodiment, via pyrophosphorolysis) of the nucleic acid hybrid occurs. The present invention focuses on embodiments wherein depolymerization is detected by the incorporation of one or more nucleotides in the depolymerized nucleic acid hybrid at the pyrophosphorylyzed end of the nucleic acid segment, as illustrated below.

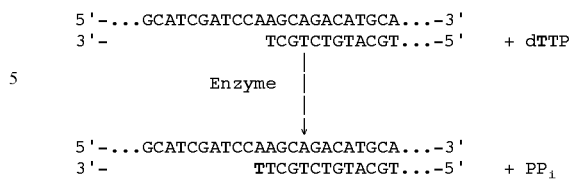

In a typical polymerization reaction, a nucleotide triphosphate is added onto the 3'-terminus of a growing nucleic acid chain. In the case of DNA, a phosphonucleotide of a deoxyribonucleoside triphosphate (dNTP) is added with the production of inorganic pyrophosphate as a side product. In the case of RNA, a phosphonucleotide of a ribonucleoside triphosphate (NTP) is added with the production of inorganic pyrophosphate as a side product.

In contrast to polymerization, in a typical pyrophosphorolysis reaction, inorganic pyrophosphate is transferred to a phosphonucleotide as the phosphonucleotide is cleaved from the 3'-terminus of a nucleic acid chain. Pyrophosphorylyzed DNA releases a dNTP, and pyrophosphorylyzed RNA releases an NTP.

In an embodiment, the present invention contemplates a method of determining whether pyrophosphorolysis of a nucleic acid hybrid occurs in a nucleic acid sample by incorporating a nucleotide in the place of a nucleotide released via pyrophosphorolysis.

Unless otherwise stated, the use of the article "a" in the patent claims follows the common patent claim construction rule that "a" means one or more than one. Thus, reference in a claim to, for example, release of a nucleotide or incorporation of a nucleotide, is intended to encompass the release or incorporation of one or more nucleotides unless otherwise stated. However, particularly in the context of pyrophosphorolysis, this is intended to cover the release of a single nucleotide or a dinucleotide, and also the repeated or stepwise release of multiple single nucleotides or dinucleotides. The mechanistic studies to date provide conflicting evidence as to whether nucleotides are released as single nucleotides or dinucleotides, but a distinction clearly exists in the art between such release of nucleotides by pyrophosphorolysis and, for example, an endonucleolytic cleavage.

B. Substrates for Nucleic Acid Detection

Various techniques are disclosed herein for ascertaining whether polymerization (nucleotide incorporation), and hence a previous depolymerization step, occurs. The presently-disclosed techniques can be applied to many situations where sequence or nucleic acid hybridization information is sought.

An important class of applications involve the sequence-specific binding of a probe to a nucleic acid target sequence. As disclosed as an embodiment in the parent cases, depolymerization via pyrophosphorylation occurs most efficiently when the 3'-terminus of the probe is bound with a high degree of complementarity to the nucleic acid target sequence.

In a subset of embodiments for determining the presence or absence of a nucleic acid hybrid, a nucleic acid hybrid is provided. In some embodiments, a nucleic acid hybrid is separately previously formed, for example prior to admixture of an enzyme and pyrophosphate to form the reaction mixture. The formation of a nucleic acid hybrid (for example by providing an olignucleotide probe capable of hybridizing with a nucleic acid target) is an additional step that is included in other embodiments. In other embodiments, a nucleic acid hybrid is formed in situ in the reaction mixture where depolymerization and incorporation of nucleotide occurs. However, hybrid formation is contemplated, for example by providing an oligonucleotide probe capable of hybridizing with a complementary nucleic acid target.

i. Nucleic Acid Probe

Some of the nucleic acid hybrid detection methods of the invention contemplate the formation of a specific nucleic acid hybrid using a nucleic acid probe that hybridizes to an essentially complementary nucleic acid target. A nucleic acid probe comprises single-stranded nucleic acid (e.g., DNA or RNA). A probe can be of varying lengths from a few to a few hundred nucleic acid residues, preferably from about 10 to 100 bases, more preferably from about 10 to about 65 bases, most preferably about 10 to 30 bases.

Preferably, a nucleic acid probe is designed to not hybridize with itself to form a hairpin structure in such a way as to interfere with hybridization of the 3'-terminal region of the probe to the target nucleic acid. Parameters guiding probe and primer design that are well known in the art apply equally well to the design or selection of probes for use with the present invention.

In a subset of embodiments of the invention, the nucleic acid probe is designed so that there can be no incorporation of a nucleotide into a strand of the nucleic acid hybrid until after pyrophosphorolysis. For example, where the 3'-terminal residue of a strand of the nucleic acid hybrid is a dideoxy (extension-blocking or chain-terminating) nucleic acid residue, extension is blocked. After such an extension-blocking residue is removed from the 3'-terminus via pyrophosphorolysis, sequence-specific nucleotide incorporation into the 3'-terminus of the pyrophosphorylyzed strand of the nucleic acid hybrid is carried out.

The invention contemplates the use of nucleotide analogs (including but not limited to inositol or any of the other available nucleotide analogs, several of which are listed in the World Intellectual Property Standard ST 25 (1998)) or modified nucleotides (including but not limited to biotinylated nucleotide as a capture label) in the construction of a nucleic acid probe.

In the design of a multiplex assay, variation of probe length, preferably by about 5 nucleic acid residues, can provide ready distinction between probes. Other methods to design readily distinguishable probes for a multiplex assay are also contemplated, including the use of a label elsewhere on the probe besides the 3'-terminal region of the probe. Further, such combinations of specific probe design methods can distinguish between two very closely related targets, such as a single nucleotide polymorphism (SNP), and even SNPs at multiple sites simultaneously.

For example, a sample is contemplated that contains DNA at a site A and a site B. Further, it is contemplated that within a given population, variation in the DNA sequence is known to exist in the DNA at sites A and B such that SNPs exist at both of these sites resulting in an allele 1 and allele 2 at both of these sites.

Probes are designed such that a 15 bp probe hybridizes to allele 1 at site A in a manner that allows pyrophosphorylation followed by incorporation to take place; a 20 bp probe hybridizes to allele 2 at site A in a manner that allows pyrophosphorylation followed by incorporation to take place; a 25 bp probe hybridizes to allele 1 at site B in a manner that allows pyrophosphorylation followed by incorporation to take place; and a 30 bp probe hybridizes to allele 2 at site B in a manner that allows pyrophosphorylation followed by incorporation to take place. Reaction of these probes as contemplated in a subset of the conditions contemplated for the invention would produce: (a) labeled products of about 15 and 25 bp if the sample only contained allele 1 DNA at site A and site B; (b) labeled products of about 20 and 30 bp in length if the sample only contained allele 2 DNA at site A and B; or (c) labeled products of about 15, 20, 25 and 30 bp in length if the sample contained both allele 1 and allele 2 DNA at sites A and B, respectively. Expansion of this reaction design to permit analysis of several additional nucleic acid targets in the same reaction mixture is contemplated using further variations of probe length, incorporated labels, or other distinguishing characteristics. Such variations can permit as many as about 50 different targets to be assayed in a single reaction mixture.

ii. Nucleic Acid Target

In an embodiment using a nucleic acid probe, a corresponding nucleic acid target sequence is a portion of a nucleic acid sample with which the probe hybridizes if that target sequence is present in the sample. A nucleic acid target is "predetermined" in that its sequence is known, thus a probe that specifically hybridizes with that target can be obtained. However, it is further contemplated that probes can be randomly generated, for example as they are for many of the nucleic acid chips used in analysis arrays. Using such designed probes, a nucleic acid target is "predetermined" in that the complementary probe sequence is known.

The determination of an appropriate nucleic acid target sequence useful for designing nucleic acid probes for use in a method of the invention is within the skill of the art. Databases of genetic sequences, such as Genbank, can be used to ascertain the uniqueness of the selected nucleic acid target. Commercially available software for designing hybridizable primers can be used to assist in the design of probes for use in the invention.

The invention contemplates the use of nucleotide analogs (including but not limited to inositol or any of the other available nucleotide analogs, several of which are listed in the World Intellectual Property Standard ST 25 (1998)) or modified nucleotides (including but not limited to biotinylated nucleotide as a capture label) in the construction of a nucleic acid target.

iii. Interrogation Position

Depolymerization reactions can be used to interrogate the identity of a specific base in a nucleic acid. For example, the identity of single base mutations, deletions, or insertions in a nucleic acid can be determined. Not all of the embodiments of the present invention utilize the interrogation position.

In one embodiment, each nucleic acid probe synthesized is substantially complementary to a target nucleic acid containing or suspected of containing a point mutation. It will be recognized that various hybridization conditions can be used, so as to vary the stringency at which hybridization occurs.

Depending on the length of the probe, the nucleotide content, and the stringency of the hybridization conditions, the probe can have mismatches in regions other than the 3'-terminal region and still hybridize sufficiently for the present invention, which is concerned with mismatches in the 3'-terminal region. In one preferred embodiment, the probe has only one base mismatch (at the single base of interest when it is not the probe designed to match that target exactly) with the target nucleic acid, and the mismatch is in the 3'-terminal region of the nucleic acid probe and the remaining bases of the probe are completely complementary to the nucleic acid target. Preferably, the single mismatch is at the 3'-terminal residue or the penultimate residue of the probe.

In preferred embodiments, a probe is designed to have a predetermined nucleotide at an interrogation position. When a complementary probe base pairs or hybridizes to a target nucleic acid, the base at an interrogation position aligns with the base in the nucleic acid target whose identity is to be determined under conditions such that base pairing can occur.

It is contemplated that an interrogation position does not have to be the 3'-terminal residue of the probe. An interrogation position is preferably within 10 bases of the 3'-terminus of the nucleic acid probe. The 10 bases are referred to herein as the 3'-terminal region of the probe. In still other preferred embodiments, an interrogation position is within 6 bases of the 3'-terminus of the nucleic acid probe. In particularly preferred embodiments, an interrogation position is at the next to last (penultimate) or last base at the 3'-terminus of the nucleic acid probe.

In preferred embodiments where the interrogation position is not at the 3'-terminal position, a probe is complementary to its predetermined target at all bases of the 3'-terminal region between an interrogation position and 3' end of the nucleic acid probe.

Typically, in a contemplated interrogation assay, the nucleic acid probes are designed so that the base at an interrogation position is complementary to the nucleotide at the predetermined position of the nucleic acid target (such as an allele), but not to other variations of that predetermined nucleic acid sequence, due to the mismatch. Likewise, a second probe can be synthesized that is complementary at an interrogation position to the nucleotide at the predetermined position of the other variations of the predetermined nucleic acid sequence (such as a different allele at that site}.

An example of an interrogation embodiment was discussed in the "Nucleic Acid Probe" section above using the designations allele 1 and allele 2. The position where the SNP occurs corresponds to the interrogation position of the nucleic acid probe.

iv. Complementarity and Mismatches

As noted in the parent applications, processes of the invention can be used to determine whether there is a match or a mismatch in the 3'-terminal region of a single or a few bases between a nucleic acid probe and a nucleic acid target sequence.

The distinction between a matched and mismatched base becomes less notable as a single mismatch is at a position further upstream from the 3'-terminal position. There is very little discrimination between a match and mismatch when a single mismatch is eleven to twelve residues from the 3'-terminal nucleotide position, whereas great discrimination is observed when a single mismatch is very near the 3'-terminus.

As disclosed in the parent application, in particular embodiments of the invention, it is desirable to include a second, destabilizing mismatch in or near the 3'-terminal region (about the last ten 3'-terminal nucleotides) of the probe, because it can enhance the discrimination between a match and a mismatch closer to the 3'-terminus (for example at the last or penultimate residue in the 3'-terminal regions, as discussed above).

v. 3' Terminus of Detection Substrate

The preferred substrate for the depolymerization and polymerization reactions is a nucleic acid hybrid having a 3'-terminus that has a 5'-overhang on the opposing strand (a recessed 3'-terminus), as illustrated above. The pyrophosphorolysis is also effective on blunt-ended nucleic acid hybrids having neither a 3' nor 5' overhang at the nucleic acid hybrid end of interest.

There are other ways to provide such a substrate besides the addition of a nucleic acid probe to a solution that may contain a nucleic acid target. There may already be a duplex nucleic acid in a sample that has the appropriate overhang. An alternative way to generate an appropriate substrate is by endonucleolytic cleavage with an endonuclease that leaves the appropriate duplex ends, as discussed in the incorporated parent cases.

C. Depolymerization and Nucleotide Incorporation Enzyme

In some embodiments, the present invention contemplates carrying out pyrophosphorolysis and incorporation of nucleotide in the same solution in a single reaction vessel. In such an embodiment, it is preferable to balance the conditions between those that favor pyrophosphorolysis and those that favor polymerization (nucleotide incorporation) of the nucleic acid strand. Several of the Examples of the invention below illustrate such conditions.

In many of embodiments of the invention contemplated, an enzyme capable of catalyzing pyrophosphorolysis is provided. In several embodiments, pyrophosphorolysis is followed by polymerization. In a subset of these embodiments, the enzyme catalyzing pyrophosphorolysis and polymerization is the same, and it is a template-dependent nucleic acid polymerase.

i. Enzymes

Template-dependent nucleic acid polymerases capable of pyrophosphorolysis include, but are not limited to, DNA polymerase $\alpha$, DNA polymerase $\beta$, T4 DNA polymerase, Taq polymerase, Tne polymerase, Tne triple mutant polymerase (Readase™, Promega Corp. Madison, Wis.), Tth polymerase, Tvu polymerase, Ath polymerase, Bst polymerase, E. coli DNA polymerase I, Klenow fragment, Klenow exo minus (exo-), AMV reverse transcriptase, RNA polymerase and MMLV reverse transcriptase. Most preferably, Klenow exo minus (Klenow exo-) or Tne triple mutant polymerase is utilized for DNA pyrophosphorolysis reactions because of their efficient utilization of 5' overhanging DNA ends.

The Tne triple mutant DNA polymerase is described in detail in WO 96/41014, whose disclosures are incorporated by reference, and its 610 residue amino acid sequence is provided as SEQ ID NO:35 of that document. That enzyme is referred to in WO 96/41014 as Tne M284 (D323A, D389A).

The thermostable polymerases are particularly preferred in embodiments of the present invention that utilize thermal cycling.

ii. Conditions for Enzyme Activity

The optimal conditions for polymerization reaction of the enzymes are well known in the art. Optimal pH ranges for such activity apply to the reactions of the present invention. The optimal conditions for the pyrophosphorylation reaction are, in general, less well known but are described in the parent patent applications, the disclosures of which are incorporated in full herein by reference. However, the present invention contemplates adjusting the reaction conditions such that neither pryophosphorylation nor nucleotide incorporation is so favored as to prevent the other reaction. Preferable pH ranges for the present invention are pH 6.0 to pH 8.0, most preferably pH 6.5 to pH 7.5. Preferred ionic strength ranges are 10 micromolar to 0.5 molar, more preferably from 10 micromolar to 100 millimolar. The template-dependent polymerases also require metal ion, typically from about 10 micromolar to 100 millimolar magnesium, but several analogs that are substitutable are known in the art and are discussed in the parent applications.

The Examples below provide a variety of useful buffers, pH, temperature and salt conditions.

iii. Suitable Nucleotide

A suitable nucleotide for incorporation into a pyrophosphorylyzed nucleic acid hybrid is one that can be added onto the 3' terminus of the pyrophosphorylyzed strand. Thus, it should be complementary or compatible with the nucleic acid residue on the opposing strand of nucleic acid, such that they will form a proper base pair in the hybrid upon its incorporation.

As such, an A will go opposite a T, and a G opposite a C, as usual, but also the invention contemplates that nucleotide analogs may be incorporated. Several nucleotide analogs are presently known, and many of the most common ones are listed in the World Intellectual Property Standard ST 25 (1998). Other nucleotide analogs are known or may later be developed that would also be useful with the present invention and are presently contemplated. A labeled or otherwise modifed nucleic acid residue is contemplated for use with the present invention. For example, the use of fluorescent or radiolabels is contemplated, as discussed herein. In addition, the use of capture labels, which as used herein refer to residues modified for attachment to a solid substrate, such as biotinylated residues that are captured on an avidin-derivatized support. Other such pairs as biotin/avidin are known in the art and are also contemplated for use with the present invention.

D. Conditions for Nucleic Acid Hybrid Detection

In preferred embodiments of the present invention, the same enzyme catalyzes both pyrophosphorolysis and polymerization. The reaction conditions are such that these opposite reactions can occur. The Examples below provide some illustrative conditions that permit both reactions to occur. A particular "balance" between pyrophosphorolysis and polymerization need not be struck between these two opposing enzyme activities. For example, the invention is also effective where the balance of conditions is closer to the polymerization side, yet sufficient depolymerization occurs to get an answer to the assay. Selection of conditions depends on the goals of the assay and many other factors in addition to the issue of what provides maximal polymerization or depolymerization activity.

Hybridization conditions can be empirically ascertained for a control sample for various time periods, pH values, temperatures, nucleic acid probe/target combinations and the like. Exemplary maintenance times and conditions are provided in the specific examples hereinafter and typically reflect low stringency hybridization conditions. In practice, once a suitable set of hybridization conditions and maintenance time periods are known for a given set of probes, an assay using those conditions provides the correct result if the nucleic acid target sequence is present. Typical maintenance times are about 5 to about 180 minutes.

In many of the contemplated processes of the present invention, a hybridization step occurs in the same solution under the same conditions at the same time as a depolymerization and a post-depolymerization polymerization step (in different probe/target hybrid complexes in that solution).

In an embodiment where a template-dependent polymerase catalyzes a pyrophosphorolysis and a polymerization reaction on a probe-target nucleic acid hybrid, the preferred conditions are, in general, slightly different from those preferred in the parent case, which focused primarily on carrying out the depolymerization.

i. Probe and Target Concentrations

In some preferred embodiments, oligonucleotide probes are typically utilized at about 100 ng to about 1 µg per 20 µL of reaction solution. That amount provides about 200 to about 1000 mass units of probe to about 1 mass unit of target weight.

In a preferred embodiment of the present invention, nucleic acid polymerase and pyrophosphate ($PP_i$) or an analogue thereof, are added to a hybridized sample containing from less than about 100 µg of target nucleic acid, to less than about 10 µg of nucleic acid. Typical target nucleic acids are present at about 1 to about 5 ng in the sample to be assayed, with a target nucleic acid length of about 30 to about 1000 bp being preferred.

ii. Enzyme Concentrations

A depolymerizing enzyme is preferably present in an amount sufficient to pyrophosphorylyze a nucleic acid hybrid to form a modified 3'-terminus. A polymerizing enzyme is preferably present in an amount sufficient to add a suitable nucleotide to a modified 3'-terminus. Preferably the depolymerizing and polymerizing enzymes are the same enzyme. That amount can vary with the enzyme used, the pyrophosphorolysis temperature, the buffer, and the like. Typical buffer and temperature conditions are discussed above.

Examples of useful enzyme concentrations are found in the examples below and the parent cases. Preferably, enzyme concentrations range from about 0.25 to about 5 units (U) of a contemplated enzyme in a 20 µL volume of reaction mixture. More preferably, for a typical reaction carried out in a 20 µL volume, about 0.25 to about 1 unit (U) of a non-thermostable enzyme such as Klenow exo- is used. More preferably, for a typical reaction carried out in a 20 µL volume, about 1 to about 5 U of the thermostable enzymes are used.

iii. Maintenance Times and Temperatures

Maintenance times are preferably long enough to provide sufficient product for analysis. Preferably a reaction mixture is maintained for about 5 to about 500 minutes, more preferably about 5 to about 180 minutes and most preferably about 15 to about 100 minutes.

The acceptable temperature ranges for maintenance of the reaction mixture during pyrophosphorolysis and nucleotide incorporation vary from reaction to reaction. Preferably the melting temperature ($T_m$) of the nucleic acid hybrid is taken into consideration when determining a useful maintenance temperature for the pyrophosphorolysis and nucleotide incorporation reactions. Preferably, maintenance temperatures are near the predicted $T_m$, typically about 50 to 60 degrees Celsius.

iv. Nucleic Acid Hybrid Turnover

A length effect was observed where shorter probes, such as about 10 to about 20 residues in length, provided more pyrophosphorylyzed and polymerized reaction product than longer probes, such as about 30 to about 65 residues. Not wishing to be bound by theory, it is suspected that this effect may be due to a lower dissociation constant with the longer complementary probes, so that there is a smaller turnover of fresh probe binding to the target.

As is illustrated in the Examples that follow, it can be beneficial to carry out a contemplated method at elevated temperatures, e.g., about 50° C. to about 90° C., and in some cases, analytical output can be enhanced by thermal cycling to accelerate probe turnover.

Thermal cycling can be used to encourage dissociation of the longer probes after permitting some time for reaction. The examples below demonstrate that thermal cycling can eliminate the length effect. Such a result is particularly useful in a multiplex reaction where probe length is varied to more easily distinguish between several simultaneous assays.

Another technique that can assist with turnover of nucleic acid hybrids, notably in the context of probe:target hybrids, is to add RecA to the reaction mixture. The *E. coli* RecA protein (Promega Corporation M1691) binds cooperatively and stoichiometrically to single-stranded DNA and is active in strand exchange as a nucleoprotein containing one RecA monomer (38 kDa) per 3 bases of ssDNA.

E. Multiplex Nucleic Acid Detection

A multiplex method of this invention is used to determine the presence or absence of a plurality of predetermined (known) nucleic acid target sequences in a nucleic acid sample.

In a multiplex method a sample to be assayed is admixed with a plurality of nucleic acid probes. The admixing of the first step is typically carried out under low stringency hybridizing conditions to form a hybridization composition. In such a hybridization composition, the 3'-terminal region of the nucleic acid probes hybridize to a nucleic acid target sequence that may be present in the sample.

The hybridization composition is maintained under hybridizing conditions for a time period sufficient to form a treated sample that may contain a plurality of predetermined nucleic acid target sequences hybridized with their respective nucleic acid probes.

When a method of the present invention is used to determine whether a particular target sequence is present or absent in a sample to be assayed, the target may be absent. When the target is absent, the resulting treated sample does not contain an appropriate template for polymerization if there was no prior depolymerization. As a result, 3' terminal residues of the probe are not released, then there is no polymerization of the depolymerized probe, and the analytical output is at or near background levels.

A contemplated method is a multiplex assay in which a plurality of probes is utilized to determine whether one or more of a plurality of predetermined nucleic acid target sequences is present or absent in a sample. As discussed in the parent cases, the probes can be designed so that a positive analytical output indicates that the target is present, or so that a positive analytical output indicates that the target is absent. For example, an unlabeled probe can be pyrophosphorylyzed to form a modified 3'-terminal region and then a suitable nucleotide having a label can be incorporated into the modified 3'-terminal region to form an incorporated modified 3'-terminal region. Analysis for the label that gives a positive analytical output means that the target was present. Alternatively, a label on a probe can be removed by pyrophosphorolysis when the target is present, resulting in a modified 3'-terminus that no longer is associated with a label. After polymerization, an assay for the label will result in a positive analytical output when the target is absent.

F. Analytical Output for Nucleic Acid Detection

The analytical output is used to determine whether or not pyrophosphorolysis has occurred. In many embodiments herein, analytical output indicated whether polymerization has occurred will indicate whether or not pyrophosphorolysis has occurred. Exemplary detection systems include various gel visualization methods, including fluorescence. These detection systems and others are discussed in the incorporated parent applications.

The fact that nucleotides were released (a qualitative determination), or even the number of nucleotides released (a quantitative determination) can be deduced through examination of the probe after depolymerization. The determination of the size of an oligonucleotide is well known in the art. For example gel separation and chromatographic separations are well known. Gel imaging techniques that take advantage of fluorescence and absorbance spectroscopy as well as radiographic methods have been described and are contemplated. Mass spectrometry of oligonucleotides is also becoming more common and are contemplated for use with the present invention.

In an embodiment of the present invention, the depolymerized probe is polymerized to incorporate one or more additional bases. An assay to determine whether the depolymerized probe is polymerized gives rise to analytical output that is used to determine whether the nucleic acid target sequence was present.

In one contemplated embodiment of the invention, the enzyme whose activity is to depolymerize hybridized nucleic acid to release nucleotides from the probe 3'-terminal end is a template-dependent polymerase, as described above. In such an embodiment, the reverse of a polymerase reaction is used to depolymerize a nucleic acid probe, and the identifier nucleotide is released when the 3'-terminal nucleotide of the nucleic acid probe hybridizes with total complementarity to its nucleic acid target sequence. A signal confirms the presence of a nucleic acid target sequence that has the sequence sufficiently complementary to the nucleic acid probe to be detected by the process of the invention.

The magnitude of a contemplated analytical output under defined conditions is dependent upon the amount of released nucleotides. Where an identifier nucleotide is released, re-polymerization of the remaining, depolymerized probe can be analyzed to provide an analytical output that has a value greater than background. Where an identifier nucleotide is not released—either because the target sequence was not present in the original sample or because the probe did not match sufficiently to become a pyrophosphorolysis substrate—the analytical output is substantially at a background level.

In some cases, it may be beneficial to enrich the nucleic acid target for hybrid formation within the nucleic acid sample. Many illustrative embodiments described in the parent applications involve detection of a gene or marker from within a massive genome, such as nucleic acid target sequences associated with blood coagulation (such as those probes associated with the Factor V Leiden mutation), probes specific to various classes of animals (such as bovine, murine, homo sapiens), congenital adrenal hyperplasia (CAH), sequences associated with cystic fibrosis, cancer-associated sequences (e.g. Bcr/Abl).

In such embodiments, it is beneficial to enrich the target sequence within the sample. A target nucleic acid sequence is amplified prior to use of the present invention. Several methods are known in the art to amplify a region of DNA. These include polymerase chain reaction (PCR), ligase chain reaction (LCR), repair chain reaction, amplification of transcripts, self-sustained sequence replication (3SR), ligation activated transcription (LAT), strand displacement amplification (SDA) and rolling circle replication. A claimed process contemplates prior treatment of a nucleic acid sample using any amplification method known in the art at the time of practicing a claimed process to detect the presence of a nucleic acid target in the sample.

i. Separation for Analysis

A great majority of the nucleic acid hybrid detection methods disclosed herein involve a separation step for analysis, most typically separation of probes incorporating a nucleotide from free nucleotides. This includes the embodiments with and without the incorporation of labels. Separation methods of the art are contemplated for use herewith, which may include, but are not limited to, electrophoretic separation or separation on a solid support (both of which are illustrated below).

Shrimp alkaline phosphatase or a related enzyme may be useful at times to alter the mobility of the nucleotides on a separation gel, as done in an example below to ascertain whether any bands were obscured. Shrimp Alkaline Phosphatase (SAP from *Pandalus borealis;* Promega Corporation M8201) catalyzes the dephosphorylation of 5' phosphates from DNA and RNA. Unlike Calf Intestinal Alkaline Phosphatase, SAP is completely and irreversibly inactivated by heating at 65 C. for 15 minutes. Alkaline phosphatases are also useful to prevent recircularization and religation of linearized nucleic acid by removing phosphate groups from both 5'-termini and may also be used for the dephosphorylation of 5' phosphorylated ends of DNA or RNA for subsequent labeling with [32P]ATP and T4 Polynucleotide Kinase. SAP is active on 5' overhangs, 5' recessed and blunt ends. The pyrophosphorolysis and nucleotide incorporation (polymerization) reactions of the present invention act on the 3'-terminus of a nucleic acid; the alteration of the 5' terminus has no effect on the pyrophosphorolysis and polymerization.

Some embodiments do not require separation, such as a flourescence energy transfer embodiment where a probe will not affect the fluorescence of a hybridizing co-analyte (or vice versa) until the fluorescence-affecting moiety (or fluorophore) has been incorporated into the probe according to the invention.

ii. Absorbance Spectroscopy

An absorbance spectrographic analysis step is contemplated to provide an analytical output, thereby provide for the determination of the presence or absence released identifier nucleotide or an incorporated suitable nucleotide, thus indicating the presence or absence of said nucleic acid target sequence. This embodiment contemplates the separation of a reaction mixture that has been treated with a depolymerizing amount of a pyrophosphorylyzing enzyme followed by polymerization and then visualization, such as on a gel. Such visualization can be by the human eye, without the need for extra equipment, such as a spectrograph.

iii. Fluorescence Spectroscopy

A wide variety of fluorescence detection methods can be used herein. In one exemplary contemplated method, an identifier nucleotide includes a fluorescent label. An identifier nucleotide can be fluorescently labeled prior to, or after, release of the identifier nucleotide. In an alternative embodiment when the nucleotide is fluorescently labeled, the analytical output is obtained by mass spectrometry.

In a preferred embodiment of the invention, the fluorescent label is part of a fluorescent analog of a nucleotide. Fluorescent nucleotide analogs are widely known and commercially available from several sources. An exemplary source is NEN Life Science Products (Boston, Mass.), who offer dideoxy-, deoxy-, and ribonucleotide analogs a labeled with fluorescein, coumarin, tetramethylrhodamine, naphthofluorescein, pyrene, Texas Red®, and Lissamine™. Other suppliers include Amersham Pharmacia Biotech (Uppsala, Sweden; Piscataway, N.J.) and MBI Fermentas, Inc. (Amherst, N.Y.).

The fluorescent label may be present on the released identifier nucleotide, or it may be present elsewhere on the interrogation probe as a marker of that probe or it may be in the incorporated suitable nucleotide. The presence of differently fluorescing analogs on different probes provides a ready means to increase the number of probes analyzable in one experiment (multiplexing). The interrogation probe may be labeled with more than one fluorescent probe thus generating mixtures of multiply-labeled probes that further increases the number of interrogation probes that can be analyzed in a single experiment.

An advantage to using fluorescent labels and fluorescence spectroscopy analysis is that there are multiple different labels available. Such different labels would be particularly useful in a multiplex embodiment of the invention. Different fluorescent labels would be used in different probes, so that the detection of a particular fluorescently-labeled nucleotide analog as a released identifier nucleotide or as an incorporated suitable nucleotide or elsewhere in the nucleic acid hybrid or nucleic acid probe could be used to deduce which nucleic acid targets are present.

For example, fluorescein has a 488 nm maximum excitation and 520 nm maximum emission wavelength, whereas rhodamine (in the form of tetramethyl rhodamine) has 550 nm maximum excitation and 575 nm maximum emission wavelength. A fluorescence detector provides an excitation source and an emission detector. The emission wavelengths of 520 nm and 575 nm are easily distinguishable using fluorescence spectroscopy.

On a per molecule basis, fluorescence spectroscopy is about 10-fold more sensitive than absorbance spectroscopy. A very wide variety of fluorescence spectroscopy-based detectors are commercially available for reading fluorescence values of single tubes, flow cells and multi-well plates, among others. For example, Labsystems Multiskan models of microplate readers are widely available with a spectral range of 400 to 750 nm, and filters for 340, 405, 414, 450, 492, 540, 620, and 690 nm (e.g. Fisher Scientific, Pittsburgh, Pa.).

It is contemplated that an incorporated suitable nucleotide could be labeled before or after incorporation using cross-linking chemistry well known in the art with commercially available reagents. For example, fluorescein isothiocyanate and rhodamine B isothiocyanate are both available from Aldrich Chemical Company (Milwaukee, Wis.). References to fluorescein isothiocyanate's use in labeling biological molecules include Nature, 193:167 (1962), *Methods Enzymol.* 26:28 (1972), *Anal. Biochem.,* 57:227 (1974), *Proc. Natl. Acad. Sci., U.S.,* 72:459 (1975).

It is contemplated that for many embodiments of the invention, it is useful to separate fluorescent nucleotides from those bound to an oligonucleotide, such as a probe. Thus, the separation techniques well known in the art and discussed above are useful with such an embodiment, including gels, capillary systems or an HPLC fitted with a fluorescence detector. The enhanced sensitivity of fluorescence relative to other spectroscopic techniques can be used to increase the sensitivity of a detection or quantification process of the invention.

G. Applications of the Detection Technology

Several applications of probe hybridization methods of determining the presence or absence of predetermined nucleic acid target sequences are disclosed in the parent cases. The presently disclosed method of ascertaining whether or not pyrophosphorolysis occurred are applicable to those methods, including the analysis of single nucleotide polymorphisms.

Methods and materials of the present invention are useful for a wide variety of applications. One notable embodiment is the detection of the presence or absence of a predetermined nucleic acid sequence in a sample using oligonucleotide probes capable of hybridizing with the predetermined nucleic acid sequence. The present invention contemplates embodiments for the detection of predetermined sequences, sensitive enough to detect a single amino acid variation in the predetermined sequence, such as a single nucleotide polymorphism (SNP). The present invention contemplates an embodiment having a multiplex format, where the presence or absence of several predetermined nucleic acid sequences may be determined at once in the same nucleic acid sample at the same time.

In yet another preferred embodiment, the probe-mediated specific nucleic acid detection method of the present invention can be used to simply identify or detect a nucleic acid of interest. For this method, nucleic acid probes (e.g., DNA or RNA) are utilized, each of which is substantially complementary to its respective target nucleic acid, which can be RNA or DNA. In a particularly preferred embodiment, each nucleic acid probe is entirely complementary to its target nucleic acid. A nucleic acid probe comprises single-stranded nucleic acid (e.g., DNA or RNA). The probe can be of varying lengths, preferably from about 10 to about 1000 bases, most preferably about 10 to 100 bases.

The ability to interrogate the identity of a specific base in a nucleic acid also permits discrimination between nucleic acids from different species, or even from different alleles.

In preferred embodiments of this method, nucleic acids with substantially identical sequences from at least two species or alleles are detected. The region of identity (target nucleic acid sequence) contains at least a single nucleotide mismatch between the species or alleles in at least one predetermined position and also contains a 3' end and a 5' end or the identification of a nucleic acid sequence unique to each species to be identified.

A method contemplated by the present invention has wide applicability in assaying nucleic acids. In some aspects, an endogenous nucleic acid is assayed to determine whether a particular native or mutant sequence is present or absent. This type of analysis is sometimes referred to as genotyping because the genetic makeup of the subject from which the nucleic acid-sample is obtained is determined. Speciation, the identity of an organism, such as the identification of a human, dog, chicken, bovine or the like can be determined by use of species-specific nucleic acid probes such as probes to selected regions of the gene encoding cytochrome B.

Using a contemplated method, one can illustratively determine whether a human patient, for example, has the Leiden Factor V mutation, a mutant β-globin gene, the cystic fibrosis-related gene in the region of the delta 508 allele, a mutation in a prothrombin gene, congenital adrenal hyperplasia, a translocation that takes place in the region of the bcr gene along with involvement of a segment of the abl gene, the number of repeated sequences in a gene such as are present in THO 1 alleles or the TPOX alleles, as well as the loss of heterozygosity of the locus of certain alleles as is found in certain cancers and also allelic trisomy. Genomic typing can also be used to assay plant genomes such as that of rice, soy or maize to determine whether they contain non-native sequences (identification of genetically-modified organisms, GMOs). The presence or absence in a sample of the genomes of microbes such as *Campylobacter jejuni*, Listeria, and *E. coli* 0H157 can be determined, and viral genomes such as that of cytomegalovirus (CMV) or human immunodeficiency virus (HIV) can be analyzed to determine whether a drug-resistant strain is present in a sample.

A contemplated method can also be utilized to assay for the presence or absence of nucleic acid that is exogenous to the source of the sample. For example, a contemplated method can be used to assay for the presence of viruses such as hepatitis C virus (HCV), cytomegalovirus (CMV), human immunodeficiency virus (HIV), as well as to determine the viral load in an organism with a disease, such as a human or a plant. A contemplated method can also be used to identify the presence of an exogenous nucleic acid sequence in a plant such as maize, soy or rice. A contemplated method can also be used to assay for the presence of microorganisms such as *Listeria monocytogenes,* Campylobacter spp., Salmonella spp., Shigella spp. or *Escherichia coli* (including *E. coli* E0157) in foodstuffs such as meats, dairy products, and fruit juices.

Another embodiment of the invention uses the nucleic acid hybrid analysis to determine nucleic acid sequences, through sequencing using pyrophosphorylation-promoted end reduction followed by base addition. Pyrophosphorolysis of the nucleic acid hybrid cleaves nucleotides from the 3'-terminus of one of the nucleic acid strands. Pyrophosphorolysis can continue after the first nucleotide is removed from the original hybrid, and then there is a new 3'-terminal residue. As earlier described, under appropriate equilibrium conditions between polymerization and pyrophosphorolysis, a suitable nucleotide can be incorporated into the depolymerized hybrid whenever that suitable nucleotide can form the appropriate base pair. In some sequencing embodiments, the nucleic acid hybrid, or a strand thereof is labeled. In some sequencing embodiments, the suitable nucleotide is labeled.

For example, when the suitable nucleotide is a fluorescent dideoxycytosine residue, then that labeled C can be incorporated into the hybrid at the 3'-terminus wherever a C is appropriate. The scheme below is a schematic representation of this process with SEQ ID NO:43 and its complements, however the pyrophosphate and released nucleotides and suitable nucleotides are omitted for brevity.

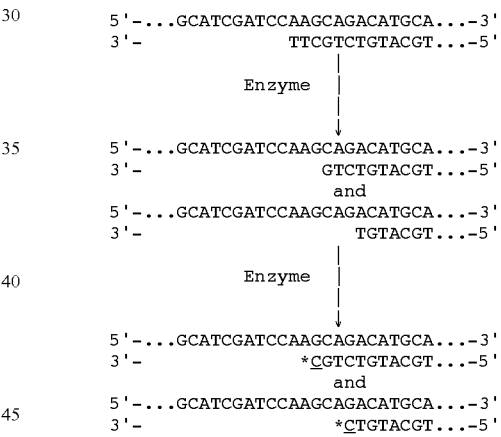

This embodiment of the invention does not require a probe to hybridize with the nucleic acid sequence of interest. For example, a cleavage of a target DNA to produce a duplex strand with a substrate 3'-terminus is also contemplated.

A multiplex embodiment is contemplated wherein multiple nucleotide ladders can be formed in the same reaction. For example by providing a differently labeled thymidine residue, the T ladder can be distinguished from the C ladder described above.

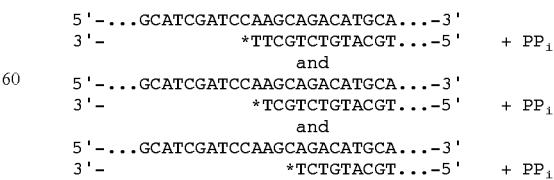

Thus, a sequencing ladder can be built up using the pyrophosphorolysis and polymerization methods of the invention.

In a subset of the sequencing embodiments of the invention, it is contemplated that the pyrophosphorylyzed nucleic acid strand be separable, for example using a capture label, such as biotin. The incorporated suitable nucleotide is derivatized with the capture label, or the capture label is elsewhere on the nucleic acid hybrid.

For example, in one embodiment of this concept, biotinylated probes are used to microsequence a nucleic acid target. This method embodiment of the invention is carried out and the 3'-terminus of the probe is pyrophosphorylyzed and one or more suitable nucleotides is incorporated into the probe. The product probes of the reaction are separated from the reaction mixture by contacting the reaction mixture with an avidin-derivatized support. The probes are then analyzed to deduce the sequence of the target nucleic acid.

Sequence determination embodiments of the invention are also contemplated that utilize nucleic acid probes. In such embodiments, the sequence of the nucleic acid target should be known sufficiently to design a probe that will hybridize. For example, such embodiments are particularly useful for determining the identity of a nucleotide, such as a particular allele in a sample where two or more possible alleles may be present. In such a contemplated use, alleles can be determined in a sample using nucleic acid probes in a sequence determination embodiment. In addition to ascertaining the identity of the nucleotide residue at the SNP position that defines the alleles of interest (e.g. the interrogation position), the suitable nucleotide may also be incorporated into the pyrophosphorylyzed probe at other sites where the nucleotide is suitable. Those additional diagnostic bands can provide confirmation that the interrogation was at the desired locus.

For example, two alleles of interest are as follows.

```
Allele A: 5'-GGA CAC TTA CCA- and

Allele B: 5'-GGA CCC TTA CCA-
```

Where the shown portion of Allele A is SEQ ID NO:44 and shown portion of Allele B is SEQ ID NO:45. Interrogation probes are designed to hybridize around the first residue in codon two of the above sequence. Labelled ddCTP is incorporated into probes using the pyrophosphorolysis reaction followed by incorporation of a suitable nucleotide. An allele A homozygote would show strong signals at lengths of primer −0, primer −2, and possibly at the primer −6 and primer −7. A homozygote of Allele B would show another band of equal strength at primer −1. A heterozygote would have the band at primer −1 that the Allele B homozygote would have but it would be half the strength of the primer −0 and primer −2 bands. Thus, in a single reaction mixture the genotype of the sample at the SNP site can be determined and the fact that the interrogation was taking place at the desired locus is confirmed by the other diagnostic bands formed.

H. Kits for Nucleic Acid Detection

Other embodiments of the invention contemplate a kit for determining the presence or absence of a nucleic acid hybrid, or a predetermined nucleic acid target sequence(s) in a nucleic acid sample. Such a kit comprises an enzyme that has pyrophosphorolysis activity and at least one nucleic acid probe, said nucleic acid probe being complementary to a nucleic acid target sequence.

Preferably the enzyme whose activity is to release nucleotides in the kit is a template-dependent polymerase that, in the presence of pyrophosphate ions, depolymerizes hybridized nucleic acids whose bases in the 3'-terminal region are complementary.

In a preferred embodiment, the enzyme capable of catalyzing pyrophosphorolysis is, but is not limited to Taq polymerase, Tne polymerase, Tne triple mutant polymerase, Tth polymerase, Tvu polymerase, Ath polymerase, T4 DNA polymerase, Klenow fragment, Klenow exo minus, *E. coli* DNA polymerase I, AMV reverse transcriptase, MMLV reverse transcriptase, or poly(A) polymerase.

The depolymerizing enzyme is preferably provided in a kit in a form that is convenient to introduce into a contemplated assay in the appropriate concentration and in a form that provides sufficient unit activity. An enzyme of a kit is typically present in an amount that conveniently permits the distribution of about 0.1 to 100 U per reaction; in particularly preferred embodiments, the concentration is about 0.5 U/reaction. In a preferred kit, an amount of enzyme sufficient to carry out at least one assay, with its controls is provided.

It is to be understood that such a kit is useful for any of the methods of the present invention. The choice of particular components is dependent upon the particular method the kit is designed to carry out (several are described above). Additional components can be provided for detection of the analytical output, such as labeled nucleotides for incorporation by polymerization into the depolymerized probe.

In one embodiment, a kit has a plurality of different nucleic acid probes that comprise fluorescent labels. In a method using such a kit, either the 3'-terminal region having incorporated suitable nucleotide or released identifier nucleotide or elsewhere on the remaining probe is detected using fluorescence spectroscopy, depending on the location of the fluorescent label within the probe. In an alternative embodiment, the released nucleotides are separated from depolymerized probes, and the remaining probe or released nucleotide is fluorescently labeled. Such an embodiment contemplates the provision of fluorescent labels and/or a magnetic nucleic acid separation medium. The above fluorescent embodiments contemplate that the fluorescent labels are distinguishable.

In another embodiment, a kit has nucleic acid probes that comprise a non-natural nucleotide analog as an identifier nucleotide. In a contemplated method using such a kit, the depolymerization is assayed for using mass spectrometry.

The kit optionally further comprises instructions for detecting said nucleic acid by depolymerization. The instructions present in such a kit instruct the user on how to use the components of the kit to perform the various methods of the present invention. These instructions can include a description of the detection methods of the invention, including detection by luminescence spectroscopy, mass spectrometry, fluorescence spectroscopy, and absorbance spectroscopy.

In one embodiment, the invention contemplates a kit for determining the presence or absence of a plurality of predetermined nucleic acid target sequences in a nucleic acid sample comprising the following components: an enzyme whose activity in the presence of pyrophosphate is to release identifier nucleotide as a nucleoside triphosphate from hybridized nucleic acid probe; pyrophosphate; and a plurality of nucleic acid probes, wherein the nucleic acid probes are complementary to their respective predetermined nucleic acid target sequence.

The enzyme whose activity in the presence of pyrophosphate is to release identifier nucleotide is as described hereinabove. Preferably, the plurality of nucleic acid probes are for related applications for a useful and convenient multiplex assay. For example, the detection of several genetic disease markers (e.g. Factor V Leiden and prothrombin), a suite of human identity screens, the detection of a series of harmful microorganisms (e.g. certain *E. coli* strains, *camphylobacter jejuni,* and salmonella or HIV-I, HIV-II, drug-resistant HIV-I, Hepatitis C and Hepatitis B), or to check a plant for a series of nucleic acids. Several examples of such probes are discussed hereinabove.

In a contemplated kit for multiplexed probe-mediated specific nucleic acid detection, the kit contains a plurality of nucleic acid probes for nucleic acid targets of interest. Preferably, where the kits contain multiple probes, each of the probes is designed to interrogate a different target DNA sequence.

The invention also contemplates kits containing instructions for use in interrogating the identity of a specific base within a nucleic acid target using a plurality of probes with different bases at the interrogation position and distinguishable probes. The invention also contemplates kits containing instructions for use in simultaneously discriminating between two homologous nucleic acid targets that differ by one or more base pairs by providing a distinguishable probe for each target. Alternatively, the invention contemplates a kit containing instructions for use in the simultaneous discrimination between a suite of nucleic acid targets that differ from a homologous nucleic acid target by one or more base pairs using distinguishable probes. The invention further contemplates a kit containing instructions for use in determining whether a sample contains a plurality of nucleic acid targets having a deletion or insertion mutation. Examples of types of nucleic acid probes that can be included in the kits and their uses are described in greater detail below.

The examples of the invention that follow are intended to illustrate selected embodiments of the present invention and should not be construed as limiting the present invention to these embodiments.

EXAMPLE 1

Fluorescent Nucleotide Incorporated into a Probe Modified by Pyrophosphorylation In the present example, a probe annealed to a target was pyrophosphorylated and then elongated by a single dideoxynucleotide. The products were examined and demonstrated to have incorporated the expected nucleotide.

Probe oligonucleotide P1A (SEQ ID NO:1) and probe oligonucleotide P2a (SEQ ID NO:2) were designed to contain a 3' cytosine residue and to hybridize with exact homology to targets T1 and T2, respectively. These probe oligonucleotides function as probes in a pyrophosphorylation reaction for which oligonucleotide T1 (SEQ ID NO:3) or T2 (SEQ ID NO:4) is the target.

oligonucleotide P2a or P1a stock solution to 45 microliter of water and 50 µl of MOPS-A (200 mM MOPS, 20 mM $MgCl_2$, pH 6.1) yielding a final concentration of 0.05 µg/µl.

Probe control solution ($P_{control}$) was assembled by mixing 50 µl of MOPS-A with 50 µl of water. Target control solution ($T_{control}$) was assembled by mixing 50 µl of denaturation solution with 50 µl of water.

Tubes were prepared in triplicate to contain 10 µl of either target T1 or target T2 or $T_{control}$. To each tube was added 10 µl of probe P1a or P2a or $P_{control}$ such that there were ultimately tubes containing each target or control with each probe or control.

The following Master Mix was assembled:

| | |
|---|---|
| 190 µl | water |
| 4 µl | READASE ™ Polymerase (Promega Corp. EAP2) |
| 12 µl | $NaPP_i$ (Promega Corp. C113) |
| 5 µl | 200 mM MOPS-A, pH 6.6 |
| 12 µl | Fluoresceira-12-ddCTP (NEL 400, Lot 090107) |

Ten microliters of the Master Mix was added to each of the tubes and they were incubated at 55° C., for one hour.

Two microliters of reaction products were combined with 1 µl of 6x gel loading buffer and loaded onto a pre-cast 20% acrylamide TBE gels (Invitrogen, Novex™, EC6315 or EC63155). The running buffer is 1x TBE diluted from the 10x stock (Promega, AA637). The gel was run until the orange G front was ~3/4 down the gel. The gels were then scanned using a Fluorimager™ and analyzed using Imagequant™. analysis software (both from Molecular Dynamics).

The results show that the negative controls, where there was no target present in the reactions, generated no specific bands on the gel. In addition, no products were seen where there was a mismatched base between the target and primer. When the matching probe and target were present (target T1 and probe P1a or target T2 and probe P2a), there were specific bands indicating incorporation of fluorescently labeled cytosine. Two labeled products are present, indicating pyrophosphorolytic activity past the first three nucleotides to the second cytosine in the probe. A high molecular weight band was also seen and was believed to be due to the non-denatured target:probe pair.

This example demonstrates that fluorescent oligonucleotides can be incorporated with high fidelity into a probe that was modified by pyrophosphorolysis.

```
P2a 5'-CGGTGCGGGCCTCTAC                                              SEQ ID NO:2

P1a 5'-CGGTGCGGGCCTCTTC                                              SEQ ID NO:1

T1  5'-ATAGCGAAGAGGCCCGCACCGATCGCCCTTCCCAACAGTTGCGCAGCCTGAATGGCGAATGGAAA   SEQ ID NO:3

T2  5'-ATAGCGTAGAGGCCCGCACCGATCGCCCTTCCCAACAGTTGCGCAGCCTGAATGGCGAATGGAAA   SEQ ID NO:4
```

Two microliters of 1 mg/ml target T1 and T2 were each diluted into 500 µl of denaturation solution (0.06 N NaOH) and 498 microliters of NANOPURE (Millipore Corp.) water yielding a final concentration of 2 µg/ml.

Probe oligo P2a and P1a stock solutions of approximately 200 µM were diluted to make working probe solutions. Working probe solutions were assembled by adding 5 µl of

EXAMPLE 2

Fluorescent Nucleotide Incorporated into a Probe When Target is Present

In the present example, a specific target is detected when a fluorescent nucleotide is incorporated into a probe, which can happen only when the target complementary to the probe is present and the probe is pyrophosphorylyzed prior to incorporation of a single, labeled dideoxynucleotide.

Probe oligonucleotide P1A (SEQ ID NO:1), probe oligonucleotide P1b (SEQ ID NO:5), and probe oligonucleotide P1c (SEQ ID NO:9) were dissolved to create a solution of approximately 200 μM in oligonucleotide. The 3'-terminus of P1b and P1c hybridize with exact homology to a segment of target oligo T1. P1c hybridizes with both T1 and T2 to the portion of those targets where they are identical, and creates a hybrid structure having a base pair mismatch 15 residues from the 3'-terminus of the P1c. Probe oligos P1a and P1b each have terminal cytosines; P1c does not. Probe oligonucleotide P1b* (SEQ ID NO:7) can hybridize with exact homology to a segment of target oligo T1 except that it contains a one base mismatch.

Probe oligonucleotide P2a (SEQ ID NO:2), probe oligonucleotide P2b (SEQ ID NO:6) each can hybridize with exact homology to a segment of target oligo T2 and both probe oligos have a terminal cytosine. Probe oligonucleotide P2b* (SEQ ID NO:8) can hybridize with exact homology to a segment of target oligo T2 except that it contains a one base mismatch and it also has a 3' terminal cytosine.

```
Probe P1b    HO-CGATCGGTGCGGGCCTCTTC         SEQ ID NO:5

Probe P2b    HO-ATCGGTGCGGGCCTCTAC           SEQ ID NO:6

Probe P1b*   HO-CGATCGGTCAGGGCCTCTTC         SEQ ID NO:7

Probe P2b*   HO-ATCGGTACGGGCCTCTAC           SEQ ID NO:8

Probe P1c    HO-TTCGCCATTCAGGCAGCGCAACTG     SEQ ID NO:9
```

The target oligos were diluted by mixing 10 μl of target oligo stock solution, 450 μl NANOPURE™ (Millipore Corp.) water, and 500 μl of denaturation solution (see Example 1) to a final concentration of 0.01 μg/μl.

The probe oligonucleotides were diluted with water to obtain a 200 μM probe oligo stock solution. Working probe solutions were made by mixing 5 μl of probe oligo stock solution, 45 μl water, and 50 μl of MOPS-A (200 mM MOPS, 20 mM MgCl$_2$, pH 6.1), to a final concentration of 10 μM.

Fourteen tubes were prepared to contain 10 μl of either target T1 or target T2 such that there were ultimately seven tubes containing each target. Tubes were further prepared to contain 10 μl of each probe (P2a, P1a, P1b, P2b, P1b*, P2b*, P1c) such that there was ultimately one tube containing 20 μl of a mix of each target and probe combination.

Fresh Master Mix was prepared as described in Example 1. The Master Mix (10 μl) was added to each of the 14 tubes and the tubes placed at 55° C. for 70 minutes. Tubes were removed from heat and loaded onto a gel, as follows: two microliters of reaction products were combined with 1 microliter of 6× gel loading buffer and loaded onto a pre-cast 20% acrylamide TBE gels (Invitrogen, NOVEX™, catalog# EC6315 or EC63155). The running buffer was 1× TBE diluted from the 10× LSS stock (Promega, AA637). The gel was run until the orange G front is ~¾ down the gel. The gels were then scanned using a FLUORIMAGER™ and analyzed using IMAGEQUANT™ analysis software (both from Molecular Dynamics).

The results showed that negative controls, where the combination was a target with a probe that was not complementary, did not generate a labeled reaction product. Where probes having a 3'-terminal cytosine that can hybridize to a target with total complementarity (exact homology) were present with the target, a labeled product resulted. In addition, products were seen in reactions containing a single mismatch. The pyrophosphorolysis reaction was not affected by a single mismatch that is 11 bases from the 3'-terminus of the probe, indicating that a mismatched base 11 bp from the 3' end of the primer in the primer-template hybrid does not prevent labeling by this technology.

EXAMPLE 3

Effect of Probe Length on Label Incorporation into a Probe

In the present example, seven different probes were pyrophosphorylyzed and then a single dideoxynucleotide was incorporated. The products were examined and demonstrated to have incorporated the expected nucleotide regardless of the total length of the probe. RecA protein is assayed for its effect on product formation.

Probe oligonucleotides P3a (SEQ ID NO:10), P3b (SEQ ID NO:11), P3c (SEQ ID NO:12), P3d (SEQ ID NO:13), P3e (SEQ ID NO:14), P3f (SEQ ID NO:15) and P3g (SEQ ID NO:16) each can hybridize with exact homology to a segment of target T3 (SEQ ID NO:17). Each probe had the identical 3-prime terminal residue, but they varied in total length from 15 to 65 base pairs.

```
P3a   HO-ACGCAAACTTTATCA                                                       SEQ ID NO:10

P3b   HO-TAAGGACGCAAACTTTATCA                                                  SEQ ID NO:11

P3c   HO-ACAGCTAAGGACGCAAACTTTATCA                                             SEQ ID NO:12

P3d   HO-TAGAAATACCACAGCTAAGGACGCAAACTTTATCA                                   SEQ ID NO:13

P3e   HO-AACTTACCAGTAGAAATACCACAGCTAAGGACGCAAACTTTATCA                         SEQ ID NO:14

P3f   HO-GTAGTAATTGAACTTACCAGTAGAAATACCACAGCTAAGGACGCAAACTTTATCA               SEQ ID NO:15

P3g   HO-ACACCAAAATGTAGTAATTGAACTTACCAGTAGAAATACCACAGCTAAGGACGCAAACTTTATCA     SEQ ID NO:16

T3    HO-AGGCTCCCCTTGATAAAGTTTGCGTCCTTAGCTGTGGTATTTCTACTGGTAAGTTCAATTACTACATTTTGGTGTGGATG SEQ ID NO:17
```

The target T3 was diluted with Nanopure™ (Millipore Corp.) water to obtain a target oligo stock solution of 1 μg/ml. Working solution was made by mixing 5 μl of target oligo stock solution, 95 μl Nanopure™ (Millipore Corp.) water, and 100 μl of denaturation solution [see Example 1] to a 0.025 μg/ml final concentration. A target control (T$_{control}$) solution was made that lacked any oligo.

Each probe nucleotide (1 mg/ml) was diluted into 50 μl of 200 mM MOPS, 20 mM MgCl2, pH 6.2 and water to produce 100 μl of working probe solution. Due to the various sizes of these probes, 5 μl of 1 mg/ml oligonucleotide stock was used for P3a, P3b and P3c; 10 μl of 1 mg/ml oligonucleotide stock for P3d, P3e and P3f; and 15 μl of 1 mg/ml oligonucleotide stock was used for P3g to create the working probe solutions.

Sixteen tubes were prepared to contain 10 μl of target. Eight tubes were further prepared to contain 10 μl of one probe (P3a, P3b, P3c, P3d, P3e, P3f or P3g) such that there was ultimately one tube containing target and each probe, plus a control tube containing only target and probe control solution (50 μl water and 50 μl MOPSA). There were 4 additional tubes containing 10 μl of probe P3b and 4 additional tubes containing 10 μl of probe P3g.

Master Mix for control reactions without a template-dependent polymerase was prepared as described in Example 1 and labeled MM-C. A second Master Mix for reactions to contain a template-dependent polymerase, (MM-D) was prepared by combining 210 μl of Nanopure™ (Millipore Corp.) water with 4 μl of Readase™ polymerase and 5 μl of MOPS-A. In addition, a 100 mM solution of ATP (E601B, 11228511) was diluted 100 fold into Nanopure™ (Millipore Corp.) water. The dilute ATP solution was used to form ATP/RecA solution, containing 5 μl of 1 mM ATP, 5μl thermostable RecA protein and 90 μl of Nanopure™ (Millipore Corp.) water.

The reaction tubes were then further prepared as follows: 10 μl of MM-C was added to tubes 1 through 8; tubes 9 and 13 received 7 μl of MM-C and 3 μl of MM-D; tubes 10 and 14 received 3 μl of MM-C and 7 μl of MM-D; tubes 11 and 15 received 1 μl of MM-C and 9 μl of MM-D such that tubes 9–11 and 13–16 had decreasing amounts of labeled nucleotide. Tubes 12 and 16 duplicated tubes 2 and 7 respectively except that they also received 10 μl of MM-C and 1 μl of ATP/RecA solution. All tubes were incubated at 55° C., and then placed at −20° C.

To visualize results, two microliter of reaction products were combined with 1 microliter of 6× gel loading buffer and loaded onto a pre-cast 20% acrylamide TBE gels (Invitrogen, Novex™, EC6315 or EC63155). The running buffer was 1× TBE diluted from the 10× LSS stock (Promega, AA637). The gel was run until the orange G front is about three-fourths of the way down the gel. They were then scanned using a Fluorimager™ and analyzed using the Imagequant™ analysis software (both from Molecular Dynamics).

The results show reaction products decreasing in mobility as the primer increases in size. The results further show that as the concentration of pyrophosphate and labeled dNTP decreases, so does the strength of the product signal. These results also show that for very long probes or for a very low concentration of label, RecA protein can enhance the level of product.

EXAMPLE 4

Specific Label Incorporation in the Presence of Other Probes

In the present example, up to four different probes were pyrophosphorylyzed and then a single dideoxynucleotide was incorporated into each pyrophosphorylyzed probe. The products were examined and demonstrated to have incorporated the expected nucleotide regardless of presence of non-homologous probes present in the reaction mixture. The present example further shows that specific products can be prepared with high fidelity in the presence of multiple probes and multiple targets.

Probe oligonucleotide P1a (SEQ ID NO:1) can hybridize with exact homology to a segment of target oligo T1 (SEQ ID NO:3). P2b* (SEQ ID NO:8) can hybridize with homology to a segment of target oligo T2 (SEQ ID NO:4), except there is a single mismatch outside of the 3'-terminal region. Probe P3d (SEQ ID NO:13) can hybridize with total complementarity to a segment of target T3 (SEQ ID NO:17). The probes vary in total length from 16 to 35 base pairs.

Working probe solution was prepared as earlier described, mixing 5 μl of probe oligo stock solution (1 mg/ml), 45 μl Nanopure™ (Millipore Corp.) water, 50 μl of MOPS-A (200 mM MOPS, 20 mM MgCl$_2$, pH 6.2). Mixed probe oligo solution, (P1a+P2b*+P3d), was comprised of 5 μl of each probe solution, 35 μl of water and 50 μl MOPS-A.

Working target oligo solution was prepared as earlier described, mixing 5 μl of target oligo stock solution, 95 μl Nanopure™ (Millipore Corp.) water, and 100 μl of denaturation solution (Promega Corp., Lot 12754503) to a final concentration of 2 μg/ml. Mixed target oligo solutions, (T3+T1) and (T3+T2) were each comprised of 5 μl of each of targets T3 and T1 or T3 and T2, respectively, with correspondingly less water to a total volume of 200 μl. Mixed target oligo solution (T1+T2+T3) was comprised of 5 μl of target T3, 2.5 μl each of T1 and T2, with corresponding less water to a total volume of 200 μl.

Three tubes were prepared to contain 10 μl of a probe solution and 10 μl of its matching target. Two tubes were prepared to contain 10 μl solution (T3+T1) and 10 μl of probe P1a and 10 μl (P1a+P2b*+P3d), separately. Two tubes were prepared to contain 10 μl solution (T3+T2) and 10 μl of probe P2b* and 10 μl (P1a+P2b*+P3d), separately. Eight tubes were prepared to contain 10 μl solution (T1+T2+T3). Three (T1+T2+T3) tubes were prepared to contain 10 μl of the individual probe solutions (P1a, P2b* or P3d). Four (T1+T2+T3) tubes were prepared to also contain 10 μl of (P1a+P2b*+P3d). There was ultimately one tube containing each probe and target combination, plus tubes containing only probe with mixed targets, and multiple probes and targets together.

Master Mix was prepared as previously described in Example 1. Ten microliter of the Master Mix was added to each of the fifteen tubes. Readase™ polymerase was serially diluted four times in 1% MOPS-A to yield 1:2, 1:4, 1:8 and 1:16 dilutions. One microliter of each of these serial dilutions was added to 4 of the tubes containing (T1+T2+T3)/(P1a+P2b*+P3d). All 15 tubes are placed at 55° C. for one hour.

To visualize results, two microliters of reaction products were combined with 1 microliter of 6× gel loading buffer and loaded onto a pre-cast 20%acrylamide TBE gels, as previously described. Gels were then scanned and analyzed as previously described.

The results show reaction products for matching probe:target pairs. In reactions containing both matching and non-matching probe:target combinations, products were seen when a probe was present with both a matching and a non-matching target; only products from combinations without a mismatched base near the 3'-end of the probe were generated. Reaction products were also seen when numerous specific and non-specific reaction reagents were present, and only specific products were generated. The mismatch present on probe oligo P2b* had no effect on the results. Decreasing the amount of READASE reduces the amount of product.

The results show that labeled product was produced in reactions containing probes and targets where the potential hybrid would contain no mismatched bases between the probe and target in the region of the last few bases of the 3' end of the probe. The addition of additional targets to a single target probe combination did not prevent the production of specific labeled product. Finally, the presence of multiple matching primer target pairs were shown to all produce the expected labeled products.

EXAMPLE 5

Effect of Shrimp Alkaline Phosphatase on the Detection of Label Incorporation

In the present example, a probe was pyrophosphorylyzed and then elongated by a single dideoxynucleotide as described earlier. The products were examined and demonstrated to have yielded the expected products only when the complementary probe and target were present together. In addition, unincorporated fluorescent nucleotides were de-phosphorylated using shrimp alkaline phosphatase to determine whether lower molecular weight bands were being obscured.

Eight reaction solutions were prepared to contain two tubes with 10 µl of either target T1 or T2, such that there were 4 tubes with each target. Tubes were further prepared, in duplicate, such that two of the T2 tubes contained probe P2a, and two of the T2 tubes contained probe P1a. The remaining tubes were prepared, in duplicate, such that two of the T1 tubes contained probe P1a, and two of the T2 tubes contained probe P1b. The reaction was permitted to proceed as described in previous examples. Reaction products were split into two tubes. One set was treated with Shrimp Alkaline Phosphatase (SAP, Promega, M8201) in order to modify the mobility of the excess labeled nucleotide by removal of the 5'-phosphate group.

Reaction products were loaded onto a gel, also as described in Example 2.

The results show reactions that contained matching (complementary) probes and target showed specific products plus the loss of non-specific staining at the bottom of the gel. No new lower molecular weight bands were observed. A non-complementary probe:target pair did not have any specific products.

EXAMPLE 6

Specific Detection of a Leiden Mutation in a Human Nucleic Acid Sample

In the present example, a labeled probe annealed to a target was pyrophosphorylyzed and then elongated by a single dideoxynucleotide as discussed previously. The products were examined and demonstrated to have incorporated the expected nucleotide.

Oligonucleotide primer FVI (SEQ ID NO:18) and oligonucleotide primer FVI' (SEQ ID NO:19) were designed to amplify a region of the Factor V (five) gene from residual anonymous DNA from either a wild-type individual, an individual with a Leiden-type mutation, or from an individual that is heterozygous for the Leiden mutation.

Interrogation probe $P_{FV}$ (SEQ ID NO:20) was designed to hybridize with perfect homology to the wild-type sequence of the Factor V gene and to contain a fluorescein label incorporated into the 5' end of the probe. Interrogation probe $P_{LM}$ (SEQ ID NO:21) was designed to hybridize with perfect homology to the Leiden mutation sequence for the same gene and to contain a rhodamine label incorporated into the 5' end of the probe.

```
Primer FVI   BtnTEG-ACCCACAGAAAATGATGCCCAG                              SEQ ID NO:18

Primer FVI'  P-TTAAGTGCAAAAAGAACAAGTAGCTTGTATTCTATAGTGTCACCTAAATC       SEQ ID NO:19

P_FV         F-CTTGAAGGACAAAATACCTGTATTCCTCG                            SEQ ID NO:20

P_LM         TMR-CTTGAAGGACAAAATACCTGTATTCCTTG                          SEQ ID NO:21
```

A mix of probes $P_{FV}$ and $P_{LM}$ was added to each of three reaction tubes containing either of three PCR products serving as targets, for the pyrophosphorolysis reaction. Master Mix for this reaction was added and the reaction allowed to proceed. Five µl of STR loading buffer (Promega Corp., DV4331) was added to the sample, and 5 µl of this was run on non-denaturing 20%polyacrylamide gel. The gel was scanned using a Hitachi FMBIO. The first scan was at 505 nanometers, illuminating the fluorescein label and the second scan was at 585 nanometers, illuminating the rhodamine label.

Results of this study indicate that the wild-type and the heterozygote target show products under the 505 nanometer scan, but no products were visible in the lane containing only mutant target. Likewise, the mutant and the heterozygote target showed products under the 585 nanometer scan, but no products were visible if only wild-type target was present. Both scans confirmed the presence of a fluorescently labeled probe. These results indicate that it is possible to measure more than one target in a single reaction, and that using differently labeled probes increases the number of interrogations possible in a single reaction.

EXAMPLE 7

Simplification of the Pattern of the Products of the Technology

In the present example, oligonucleotides complementary to the probes (designated shifters) are used to alter (shift) the mobililty of the products produced using the technology such that they occupy less of the resolution area of non-denaturing gels. Such a reduction in the space occupied by any one set of products on the gel should allow a larger number of products to be individually visualized on one gel, thus increasing the level of multiplexed analysis that can be analyzed at one time. The shifters are added after the reaction has been terminated by addition of the commonly used metal chelator EDTA to a concentration in excess of the magnesium in the reaction. This prevents the shifters from acting as a template. The shifters are added in a molar excess of the total concentration of primer added to the reaction to allow all of the primer (both reacted and unreacted) to hybridize to the added oligonucleotide. In addition, the terminated reaction with the shifter added is heated to disrupt any primer-template hybrids in the solution and then cooled to allow the primer to hybridize to the shifter.

Probes P1a and P2a and Targets T2 and T1 are the same as in Example 1. Each probe (10 μl) was mixed 10:200 in Nanopure™ (Millipore Corp.) water and MOPS-A to obtain a final concentration of 100 mM MOPS, 10 mM $MgCl_2$.

Probes and targets were prepared as earlier described. In addition two new oligonucleotides designated shifter oligonucleotides, S1,2a (SEQ ID NO:22) and S1,2b (SEQ ID NO:23) were designed to hybridize with probes P2a and P1a. The shifters are identical except that shifter S1,2a is 6 nucleotides longer than shifter S1,2b. Shifter oligos were prepared in EDTA-containing buffer (0.1 mM EDTA, final concentration). A small amount of shifter oligo was also prepared in EDTA-free buffer.

```
S1,2a  HO-ATAGCGAAGAGGCCCGCACCGATCGCC   SEQ ID NO:22

S1,2b  HO-ATAGCGAAGAGGCCCGCACCG         SEQ ID NO:23
```

Two tubes were prepared to contain either 20 μl of probe P2a and 20 μl of its matching target, T2, or 20 μl of probe P1a and 20 μl of its matching target, T1. Master mix was prepared as in Example 1. 20 μl of Master Mix was added to each of the two tubes, they were incubated at 55° C. for one hour, and then stored at minus 20° C.

Ten tubes were prepared such that 5 each contained 4 μl of each probe/target combination. To each of 4 of the probe/target combinations, 1 μl of one of the shifter oligos was added, such that the 4 tubes each contained one probe, its matching target and one of the shifters. The concentration of shifters must be such that it is in Molar excess with respect to the interrogation probes to ensure that all the labeled probe is uniformly shifted. These were heated at 95° C. for 2 minutes, then permitted to cool to room temperature. The heating step was only necessary because the samples had been earlier frozen.

Four of the remaining tubes were prepared as above, except that after cooling to room temperature, the samples were precipitated using 5 μl of 2M ammonium acetate (pH 4.6) and 90 μl of 100% ethanol, then incubated at minus 20° C. for about 20 minutes. The last two tubes were prepared with the shifter S1,2b, which had been prepared in EDTA-free buffer, and precipitated as above. Precipitated samples were resuspended. Gels were prepared as described in Example 1.

The results show that without the addition of shifters, multiple products are resolved in the gel for each reaction. In the samples treated with shifters as described above, only one major product is seen on the gel at a mobility dependent upon the length of the shifter added. Thus shifters can alter the mobility of the reaction products on the gel to a new location dependent upon the length of the shifter used and that they can be used to reduce the number of separate products species seen, thus increasing the number of different interrogation products that can be separately observed in one lane of a gel. In particular, these results specifically show that using shifters, one can achieve a product homogeneity in cases where two products are formed due to closely-spaced identical nucleotides (for example a "C" at the 3' terminus and at the minus 4 position). These results also indicate that EtOH precipitation may help to reduce the amount of free label present in a sample relative to the amount of product seen, and that EDTA does not seem to affect the labeled products seen from the reaction.

EXAMPLE 8

Specific Detection of the Congenital Adrenal Hyperplasia gene in Humans

This example demonstrates that the technology can be used for determining the genotype of DNA segments that are associated with the human genetic disease known as Congenital Adrenal Hyperplasia (CAH). In addition, it was used to explore the effect of target concentration and NaOH concentration used to dilute the target on the amount of product made. Finally, a time course following the production of specific labeled primer products from probes designed to interrogate alleles associated with congenital adrenal hyperplasia was performed. The probes were designed to hybridize with total complementarity to one of four targets, all targets being different fragments of the same gene, the CAH gene (associated with congenital adrenal hyperplasia). The probe:target pairs are: P6-T6, P4-T4, P5-T5, P7-T7. The probes were pyrophosphorylyzed and then elongated by a single dideoxynucleotide as before. The products were examined and demonstrated to yield the expected products with high specificity. In addition, the data indicate that slightly changing the reaction pH by decreasing the concentration of the sodium hydroxide used to generate the working target solution did not affect the specificity of the reaction. Decreasing the amount of target in the reactions was shown to decrease the amount of labeled primer produced. The time course performed indicated that produce accumulation continued over the entire 60 minutes of the reaction incubation.

```
                                          SEQ ID NO:24
P4  HO-CACCCTCCAGCCCCCAAC

SEQ ID NO:25
P5  HO-CACCCTCCAGCCCCCACC

SEQ ID NO:26
P6  HO-CCCTCCAGCCCCCAGC

SEQ ID NO:27
P7  HO-TCTCTCCTCACCTGCAGCATCAAC

SEQ ID NO:28
T4  HO-AGGAGTTGGGGGCTGGAGGGTGGGAA

SEQ ID NO:29
T5  HO-AGGAGGTGGGGGCTGGAGGGTGGGAA

SEQ ID NO:30
T6  HO-AGGAGCTGGGGGCTGGAGGGTGGGAA

SEQ ID NO:31
T7  HO-GTAACAGTTGATGCTGCAGGTGAGGAGAGAA
```

Target oligonucleotides were prepared with Nanopure™ (Millipore Corp.) water to a concentration of approximately 1 mg/ml. Working target solutions were made by mixing target oligo stock solution (5 μl), water (10 μl), and 2× denaturation solution (60 mM NaOH) to a final concentration of 25 ng/μl in 0.03 N NaOH denaturation solution, as previously described. Target T4 was further prepared to provide the following: T4-1 was at 25 ng/µl in 0.015 N NaOH; T4-2 was at 25 ng/µl in 0.006 N NaOH; and T4-3 was at 5 ng/µl in 0.03 N NaOH.

The probe oligonucleotides were diluted in Nanopure™ (Millipore Corp.) water to a final concentration of 1 mg/ml. Working probe solutions were made by mixing probe, water and 2× MOPS (as previously described) to a final concentration of 50 µg/ml in MOPS-A (100 mM MOPS, 10 MM $MgCl_2$, pH 6.1).

Four tubes were prepared to contain 10 µl of each probe and 10 µl of its matching target. Three tubes were prepared with 10 µl of probe P4 and 10 µl of one of the targets T4-1, T4-2 or T4-3. Two tubes were prepared with 25 µl of P4 and either 25 or 5 µl of T4, the balance of volume in the tube given 5 µl of T4 being made up by Nanopure™ (Millipore Corp.) water. These two tubes are labeled 8 and 9. Lastly, eight tubes were prepared containing only 1 µl of 0.5M EDTA. These were labeled "8T0" through "8T3", and "9T0" through "9T3".

Master Mix was prepared as previously described in Example 1. 10 µl of Master Mix was added to the first 7 tubes, and tubes were placed at 55° C.

25 µl of Master Mix was added to tubes 8 and 9 and mixed. Immediately, 10 µl from tubes 8 and 9 were transferred to tubes 8T0 or 9T0; ($t_0$=zero minutes at 55 C.), and tubes 8 and 9 were placed at 55° C. After 15 minutes of incubation at 55 C., another 10 µl was removed from tubes 8 and 9 and transferred to tubes 8T1 and 9T1 ($t_1$=15 minutes), and incubation continues. After 30 minutes of incubation at 55 C., a third 10 µl aliquot was removed from tubes 8 and 9 and transferred to tubes 8T2 and 9T2 ($t_2$=30 minutes) and incubation continues. At 45 minutes a fourth 10 µl aliquot was removed from the reaction tubes 8 and 9 and transferred to tubes marked 8T3 and 9T3 ($t_3$=45 minutes) and incubation continued. At 60 minutes, all tubes are removed from the heater and placed at minus 20° C.

Gel electrophoresis was carried out as earlier described. The results show that labeled products were produced in the reactions containing matching probe:target pairs and indicate that there is no apparent effect on the amount of product made as a result of the slight pH change produced in the reaction by altering the concentration of sodium hydroxide used in the target solution. In addition, the results show that reducing the level of target reduces the amount of product produced. Finally examination of the samples taken at 0, 15, 30, 45 and 60 minutes indicates that product continued to accumulate over the entire time period of the incubation, so as the reaction time is extended, the amount of product formed can be increased.

EXAMPLE 9

Effect of the Concentration of Probe or Target on the Assay

In the present example, the concentration of probe or target present was varied in the reaction and they were held at constant temperature. The products were examined and demonstrated to have yielded the expected products, with increasing amount of target or probe having a positive effect on the visibility of reaction products on a gel.

A "1×" probe solution, designated P3b in the table below, was produced by diluting 5 µl of a 1 mg/ml oligonucleotide stock of P3b (Sequence ID NO:11) with 45 µl of water and 50 µl of MOPS A (see Example 1). Solution P3bx2 was prepared by dilution 10 µl of the 1 mg/µl P3b stock with 40 µl of water and 50 µl of MOPS A. Solution P3bx4 was prepared by diluting 20 µl of the 1 mg/ml solution of P3b with 30 µl of water and 50 µl of MOPS A.

Template (target) solution T was prepared by diluting 5 µl of stock oligonucleotide T3 (1 mg/ml)(sequence ID NO:17) with 95 µl of water and 100 µl of denaturation solution (60 mM sodium hydroxide). Template solution T3×2 was prepared as was solution T except that 10 µl of stock oligonucleotide was used and the water reduced to 90 µl. Template solution T3×4 was prepared as was solution T except that 20 µl of the stock oligonucleotide was used and the water reduced to 80 µl.

Master mix was assembled as in Example 1 and the reactions shown in the table below were assembled and incubated at 55° C. for 60 minutes.

| Tube | Probe (µl) | Target (µl) | MM (µl) | Temp (° C.) | Time (min) |
|---|---|---|---|---|---|
| 2 | 10 of P3b × 2 | 10 of T3 × 02 | 10 | 55 | 60 |
| 5 | 10 of P3b | 10 of T3 × 02 | 10 | 55 | 60 |
| 6 | 10 of P3b × 2 | 10 of T3 × 02 | 10 | 55 | 60 |
| 7 | 10 of P3b × 4 | 10 of 3T3 × 02 | 10 | 55 | 60 |
| 1 | 10 of P3b × 2 | 10 of T3 | 10 | 55 | 60 |
| 3 | 10 of P3b × 2 | 10 of T3 × 4 | 10 | 55 | 60 |
| 4 | 10 of P3b × 2 | 10 of T3 × 1 | 10 | 55 | 60 |

The products produced were visualized by gel electrophoresis and fluorometry as described in Example 1. The results indicate that the concentration of either primer or target does not affect the specificity of the technology, but may affect amounts of products seen on the gel. In this case, increasing concentration of the primer may increase the signal strength of the product, and decreasing concentration of the target may decrease signal strength. Optimization of these concentrations may depend upon the nature of the probe:target pair, as has been observed in the art using other nucleic acid hybrid detection methods.

EXAMPLE 10

Effect of Thermal Cycling

This Example demonstrates how thermal cycling is useful for enhancing the sensitivity of nucleic acid detection by encouraging dissociation of reacted probe from the target, permitting unreacted probe to bind. In the present example, working solutions of probes P3d and P3b (made as in Example 3) were diluted in MOPS buffer, as earlier described. Stock oligonucleotide solution T3 (from Example 1) was diluted in 300 µl of denaturation solution and 495 µl water to form solution T3A. A second target solution was prepared such that the target was present at a final dilution of 1:5, T3B.

Tubes were prepared to contain 50 µl of each target and each buffer, such that there were 4 tubes, labeled 1 through 4, with each target dilution present with each of the two probes. Two additional sets of tubes labeled 1 through 4 were also prepared.

The Master Mix was assembled as previously described, and 50 µl of the Master Mix was added to each of the four tubes. The reactions were separated into three separate tubes. One set of 4 tubes were permitted to incubate at 55°

C. for one hour. A second set of 4 tubes was thermally cycled for 5 minutes at about 55° C., followed by 5 minutes at 75° C., six times. The third set of 4 tubes was thermally cycled for 1 minute at about 55° C., followed by 1 minute at 75° C., thirty times.

The results show that low target concentrations produce less labeled product formation under any of the three reaction conditions. The shorter probe (P3b) provided more product under these conditions. Under certain conditions, thermal cycling increases the rate of product formation. These conditions can be optimized based upon the nature of the probe and the target without undue experimentation.

EXAMPLE 11

Thermal Cycling Equalizes the Length Effect of Short and Long Probes

The present example shows that thermal cycling can be used to encourage dissociation of probes from the targets after reaction. In some examples, a "length effect" was noted such that more reaction product was observed for shorter probes than longer probes. Not wishing to be bound by theory, it was suggested that the length effect was because

EXAMPLE 12

Conditions For Detection May Vary Depending upon the Nucleotide Composition of the Assayed Nucleic Acid Hybrid This example shows that, although fluorescent oligonucleotide incorporation is specific, conditions for detection of the nucleic acid hybrid via pyrophosphorolysis and incorporation of nucleotide methods varies predicted melting temperature of the probe/target nucleic acid hybrid and can be ascertained without undue experimentation. Two probes were designed to hybridize to a target oligo with a preferred melting temperature, both targets being different fragments of the same gene, the CAH gene (associated with congenital adrenal hyperplasia). The probe target pairs are: P8-T8 and P9-T9. The probes were pyrophosphorylyzed and then a single dideoxynucleotide was incorporated into the probe, the reaction taking place either at constant temperature or in a thermal cycling protocol as discussed previously. The products were examined and demonstrated to yield the expected products with high specificity.

```
P8  HO-TCCTCCGGATCAATCCCCAGATTCAGCAGCGACTGC           SEQ ID NO:32

P9  HO-ACTCCTCCGGATCAATCCCCAGATTCAGCAGCGACTGT         SEQ ID NO:33

T8  HO-ACCTGCAGTCGCTGCTGAATCTGGGGAATGATCGGGAGGAGTCCTGC  SEQ ID NO:34

T9  HO-ACCTACAGTCGCTGCTGAATCTGGGGAATGATCGGGAGGAGTCCTGC  SEQ ID NO:35
``` the shorter probes dissociated more readily than the longer probes, permitting more unreacted probe to have access to the target, and thus more product formation. The length effect may be minimized by thermal cycling to encourage similar dissociation of both short and long probes. The use of a thermostable template-dependent polymerase as the enzyme catalyzing pyrophosphorolysis and nucleotide incorporation is preferred in such an embodiment. Further, the incorporation of mismatches into certain parts of the longer probes may affect the melting temperature of the hybrid pair.

In the present example, probes of various sizes were annealed to a target and permitted to undergo pyrophosphorylysis either under constant temperature conditions or thermal cycling conditions as discussed before.

A set of six tubes was prepared in duplicate, totaling twelve tubes. Target solution T3A was prepared as in Example 10. Probes P3a, P3c, P3d, P3e, P3f and P3g were also prepared as earlier described, in a MOPS solution (as described in Example 3).

Tubes were prepared in duplicate such that each tube contained 10 µl of target solution, and two tubes each contained 10 µl of one of the probes.

Master mix was prepared as earlier described, and 10 µl was added to each of the 12 tubes, above. One set of six tubes was incubated at 55° C. for one hour. The second set of tubes was incubated at 55° C. for 4 minutes and 45 seconds followed by 14 seconds at 85° C., and cycled for one hour.

The results show that generally, for the longer probes, product formation is enhanced when the reaction is thermally cycled. Optimization of thermal cycling does not require undue experimentation.

Targets and probes were prepared in solutions as described earlier. Four tubes were prepared in duplicate such that there are two sets of tubes, with two each containing a probe and target pair.

Master Mix was prepared as described earlier, except that a fluorescent guanosine is the labeled nucleotide. Ten µl of the Master Mix (G) was added to each tube, and one set of tubes was incubated at 55° C. for one hour, and the second set of tubes was incubated as in Example 11.

The results indicate that in the absence of the appropriate probe:target pair, there is no product formation. The results also indicate that some optimizing may be necessary for particular probes. This finding is a reasonable expectation, because nucleotide content directly influences hybridization optimization. For example, mismatched bases could be deliberately incorporated into longer probes to allow for a desired melting temperature of the hybrid pair.

EXAMPLE 13

Conditions For Detection of the Assayed Nucleic Acid Hybrid II

The present example is very similar to Example 12, but uses different probe:target pairs. Two probes were designed to hybridize to a target oligo with a preferred melting temperature, both targets being different fragments of the same gene, the CAH gene (associated with congenital adrenal hyperplasia). The probe target pairs are: P10-T10 and P11-T11. The probes were pyrophosphorylyzed and then elongated by a single dideoxynucleotide, the reaction taking place either at constant temperature or in a thermal cycling protocol as discussed before. The products were examined and demonstrated to yield the expected products with high specificity.

```
P10  HO-GCCCTTGGTCAATCCCACGATCGCCGAGGTGCTGCGCCTGCGG          SEQ ID NO:36

P11  HO-GCCCTTGGTCAATCCCACGATCGCCGAGGTGCTGCGCCTGTGG          SEQ ID NO:37

T10  HO-AACGGGCCGCAGGCGCAGCACCTCGGCGATGGTGGCATTGAGCAAGGGCA   SEQ ID NO:38

T11  HO-AACGGGCCACAGGCGCAGCACCTCGGCGATGGTGGCATTGAGCAAGGGCA   SEQ ID NO:39
```

Targets and probes were prepared in solutions as described previously. Four tubes were prepared in duplicate such that there were two sets of tubes, with two each containing a probe and target pair.

A Master Mix was prepared as described before, with a fluorescent guanosine as the labeled nucleotide. Ten μl of the Master Mix (G) is added to each tube, and one set of tubes was incubated at 55° C. for one hour, and the second set of tubes was incubated as in Example 11.

The results show that in the absence of the appropriate probe:target pair, there is no product formation. The results also confirm that some optimizing may be necessary as described earlier.

EXAMPLE 14

Nucleic Acid Hybrid Detection Using a Solid Support for One Hybrid Strand

This example demonstrates one embodiment of a nucleic acid hybrid detection method using a solid support to grasp one strand of the nucleic acid hybrid. A solid support, a TETRALINK resin (Promega catalog number B259), was prepared such that it was bound with oligo probe number P12. This probe also contains a biotinylated moiety (Btn-) at the 5' end. Two target probes were prepared such that one would match with perfect homology to probe P12 (Target T12) and the other T12*.

```
                                                   SEQ ID NO:40
P12   Btn-CCTCTTCGCTATTACTTCGCCATTTGACGTTGGAG

SEQ ID NO:41
T12   HO-GAGTTCTCCAACGTCAAATGGCGAACATTA

SEQ ID NO:42
T12*  HO-GAGTTCGCCAACGTCAAATGGCGAACATTA
```

The resin was prepared according to manufacturer's instructions, in brief, 200 μl of resin was placed on a BIO-RAD poly-prep column and washed with 10 ml of nuclease-free water. The column was then equilibrated with 10 ml of 50 mM Tris-HCL pH 7.5/0.1% Tween 20. After most of the equilibration buffer had passed through the column, 100 μl of probe P12 at 1 mg/ml was placed on the column. The resin was mixed briefly with a Pasteur pipet and permitted to incubate for 15 minutes at room temperature. The column was then washed with 10 ml of 10 mM Tris-HCL (w/o Tween), followed by 10 ml of nuclease-free water. Oligo-resin was then transferred to a microfuge tube.

Two hundred microliter of resin was mixed with 200 μl of neutralization solution (200 mM MOPS, 6.15; 20 mM $MgCl_2$).

Targets were prepared such that 50 μl of T12 and T12* (at 1 mg/ml) were added to 50 μl of nuclease free water, in duplicate, such that there were two tubes of each target.

Master Mix was prepared with 190 μl of NANOPURE water, 5 μl of MOPS-A (200 mM MOPS, 20 mM $MgCl_2$, pH 6.1), 8 μl of $NaPP_i$ (40 mM), 5 μl F-12-ddCTP, and 2 μl of READASE™ Polymerase (Promega EAP#2) or 2 μl of nuclease free water.

Fifty microliters of labeled resin were added to each of the four tubes containing target. To one set of tubes (one of each target) was added 100 μl of the Master Mix, and to the second set of tubes was added 100 μl of control Master Mix (no enzyme). All tubes were permitted to incubate at 55° C. for one hour.

After incubation, contents of each tube were placed into separate fresh poly-prep columns (BIO-RAD) and washed with 50 mM Tris-HCL (20 ml). Resin was then examined under an inverted fluorescent microscope. The data indicate that all beads labeled with probe P12 and that those later incubated with its matching target T12 were fluorescent. Resin beads labeled with probe P12 and incubated with a target containing mismatches, T12*, do not show labeling that is significantly higher than background. Likewise, in the presence of READASE™, there is no significant labeling of the bead, regardless of target used.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

---

What is claimed is:

1. A method for determining the presence or absence of a nucleic acid hybrid in a sample comprising the following steps:
   (a) providing a reaction mixture comprising (i) a sample that may contain a nucleic acid hybrid that comprises a 3'-terminus, (ii) pyrophosphate, (iii) an enzyme that catalyzes the release of a nucleotide from a nucleic acid hybrid, by pyrophosphorolysis of the 3'-terminus of a strand of the nucleic acid hybrid in the presence of pyrophosphate, and (iv) a suitable nucleotide that can be incorporated in the place of said released nucleotide;
   (b) maintaining said reaction mixture for a time period and under conditions that permit (i) pyrophosphorolysis of the 3'-terminus of a strand of a nucleic acid hybrid to produce a released nucleotide and a modified 3'-terminus as well as (ii) the incorporation of said suitable nucleotide into the modified 3'-terminus of the nucleic acid hybrid to produce an incorporated modified 3'-terminus, thereby forming a treated sample; and
   (c) assaying the treated sample to determine whether incorporation of said suitable nucleotide into the hybrid occurred and thereby determining the presence or absence of a nucleic acid hybrid in said sample.

2. The method of detecting the presence or absence of a nucleic acid hybrid according to claim 1 wherein the nucleotide suitable for incorporation into the modified 3'-terminus of the nucleic acid hybrid includes a label.

3. The method of detecting the presence or absence of a nucleic acid hybrid according to claim 1 wherein the method of assaying whether incorporation of a suitable nucleotide occurred comprises determining whether the label is associated with the nucleic acid hybrid.

4. The method of detecting the presence or absence of a nucleic acid hybrid according to claim 2 wherein the label is a fluorescent label.

5. The method of detecting the presence or absence of a nucleic acid hybrid according to claim 3 wherein determining whether the fluorescent label is associated with the nucleic acid hybrid comprises the following steps:
   (a) providing a treated sample comprising a fluorescence-modulating oligonucleotide that comprises a fluorescence quencher or enhancer that is complementary to the incorporated modified 3'-terminus having the fluorescent label;
   (b) maintaining the treated sample under conditions and for a time period sufficient to permit hybridization of said incorporated modified 3'-terminus with said fluorescence-modulating oligonucleotide to form a fluorescence-modulated hybrid;

(c) irradiating the treated sample with radiation that is appropriate for causing fluorescence of said label; and (d) monitoring the fluorescence of said treated sample comprising a fluorescence-modulating oligonucleotide, whereby a difference in fluorescence indicates the presence of a fluorescence-modulated hybrid and therefore said nucleic acid hybrid in the sample.

6. The method of detecting the presence or absence of a nucleic acid hybrid according to claim 1 wherein said nucleic acid hybrid is formed between a target nucleic acid strand and a probe nucleic acid strand.

7. The method of detecting the presence or absence of a nucleic acid hybrid according to claim 2 wherein the label is a capture label.

8. The method of detecting the presence or absence of a nucleic acid hybrid according to claim 1 wherein said nucleic acid hybrid comprises a label.

9. The method of detecting the presence or absence of a nucleic acid hybrid according to claim 8 wherein said label is a capture label.

10. The method of detecting the presence or absence of a nucleic acid hybrid according to claim 2 wherein said nucleotide suitable for incorporation into the modified 3'-terminus of the nucleic acid hybrid is a chain terminating or other polymerization-blocking nucleotide.

11. The method of detecting the presence or absence of a nucleic acid hybrid according to claim 6 wherein assaying to determine whether incorporation of said suitable nucleotide occurred is carried out by detecting an increase in the length of said probe.

12. A method for determining the presence or absence of a nucleic acid target in a sample comprising the following steps:

(a) providing a reaction mixture comprising (i) a sample that may contain a nucleic acid target, (ii) a nucleic acid probe corresponding to said nucleic acid target, (iii) pyrophosphate, (iv) an enzyme that catalyzes the release of a nucleotide from a nucleic acid hybrid, which comprises a 3'-terminus, by pyrophosphorolysis of the 3'-terminus of a strand of the nucleic acid hybrid in the presence of pyrophosphate, and (v) a suitable nucleotide that can be incorporated in the place of said released nucleotide;

(b) maintaining said reaction mixture for a time period and under conditions that permit (i) hybridization of the nucleic acid target with the nucleic acid probe to form a nucleic acid hybrid that comprises a 3'-terminus, (ii) pyrophosphorolysis of the 3'-terminus at a strand of a nucleic acid hybrid to produce a released nucleotide and a modified 3'-terminus as well as (iii) the incorporation of said suitable nucleotide into the modified 3'-terminus of the nucleic acid hybrid to produce an incorporated modified 3'-terminus, thereby forming a treated sample; and (c) assaying the treated sample to determine whether incorporation of said suitable nucleotide occurred and thereby determining the presence or absence of the nucleic acid target in said sample.

13. The method for determining the presence or absence of a nucleic acid target in a sample according to claim 12 wherein said reaction mixture may comprise a plurality of nucleic acid targets and their corresponding nucleic acid probes.

14. The method for determining the presence or absence of a nucleic acid target in a sample according to claim 13 wherein said nucleic acid probes are distinguishable from one another on the basis of length, thereby permitting the determination of the presence or absence of a plurality of nucleic acid targets.

15. The method for determining the presence or absence of a nucleic acid target in a sample according to claim 13 wherein the suitable nucleotides incorporated to form the incorporated modified 3'-terminus permit distinction between the probes, thereby permitting the determination of the presence or absence of a plurality of nucleic acid targets.

16. The method for determining the presence or absence of a nucleic acid target in a sample according to claim 15 wherein the nucleic acid probes having incorporated modified 3'-termini are distinguishable from one another on the basis of the suitable nucleotide incorporated or on the basis of length, thereby permitting the determination of the presence or absence of a plurality of nucleic acid targets.

17. The method for determining the presence or absence of a nucleic acid target in a sample according to claim 12 wherein said reaction mixture may comprise a plurality of nucleic acid targets that differ from one another by a single base.

18. The method for determining the presence or absence of a nucleic acid target in a sample according to claim 17 wherein said plurality of nucleic acid targets differ from one another by a single base at an interrogation position.

19. The method for determining the presence or absence of a nucleic acid target in a sample according to claim 18 wherein the penultimate 3'-terminal residue of the corresponding nucleic acid probe base pairs with the interrogation position of the nucleic acid target.

20. A method for determining the presence or absence of a specific nucleic acid base at an interrogation position of a nucleic acid target in a sample comprising the following steps:

(a) providing a reaction mixture comprising (i) a sample that may contain a nucleic acid target having a nucleic acid residue at an interrogation position, (ii) a nucleic acid probe comprising a nucleic acid residue in its 3'-terminus that base pairs with the interrogation position of the nucleic acid target when the nucleic acid target and the nucleic acid probe are hybridized to form a nucleic acid hybrid, (ii) pyrophosphate, (iii) an enzyme that catalyzes the release of a nucleotide from a nucleic acid hybrid, which comprises a 3'-terminus, by pyrophosphorolysis of the 3'-terminus of a strand of the nucleic acid hybrid in the presence of pyrophosphate, and (iv) a suitable nucleotide that can be incorporated in the place of said released nucleotide;

(b) maintaining said reaction mixture for a time period and under conditions that permit (i) formation of a nucleic acid hybrid between the nucleic acid probe and the nucleic acid target, (ii) pyrophosphorolysis of the 3'-terminus of a strand of a nucleic acid hybrid to produce a released nucleotide and a modified 3'-terminus and (iii) the incorporation of said suitable nucleotide into the modified 3'-terminus of the nucleic acid hybrid to produce an incorporated modified 3'-terminus, thereby forming a treated sample; and (c) assaying the treated sample to determine whether incorporation of said suitable nucleotide occurred and thereby determining the presence or absence of a specific nucleic acid base at an interrogation position of a nucleic acid target in said sample.

21. The method for determining the presence or absence of a specific nucleic acid base at an interrogation position of a nucleic acid target in a sample according to claim 20 wherein the nucleic acid residue of the nucleic acid probe that corresponds with the interrogation position of the nucleic acid target is the 3'-terminal residue.

22. The method for determining the presence or absence of a specific nucleic acid base at an interrogation position of a nucleic acid target in a sample according to claim 20 wherein the nucleic acid residue of the nucleic acid probe that corresponds with the interrogation position of the nucleic acid target is the penultimate 3'-terminal residue.

23. A reaction mixture comprising (i) a sample that may contain a nucleic acid hybrid that comprises a 3'-terminus, (ii) pyrophoaphate, (iii) an enzyme that catalyzes the release of a nucleotide from a nucleic acid hybrid, which comprises a 3'-terminus, by pyrophosphorolysis of the 3'-terminus of a strand of the nucleic acid hybrid in the presence of pyrophosphate, and (iv) a suitable nucleotide that can be incorporated in the place of said released nucleotide.

24. The method for determining the presence or absence of a nucleic acid hybrid in a sample according to claim 1 wherein said nucleic acid hybrid is affixed to a solid support.

25. The method for determining the presence or absence of a nucleic acid hybrid in a sample according to claim 24 wherein said nucleic acid hybrid is affixed to a solid support through attachment of a strand of the nucleic acid hybrid to said solid support.

26. The method of detecting the presence or absence of a nucleic acid hybrid according to claim 9 wherein said nucleic acid hybrid is attached to a solid support through said capture label and wherein said suitable nucleotide is a different label used for assaying the treated sample to determine whether incorporation of said suitable nucleotide occurred.

27. A method of determining a nucleotide sequence of a nucleic acid hybrid that comprises the following steps:

(a) providing a reaction mixture comprising (i) a sample contains a nucleic acid hybrid that comprises a 3'-terminus, (ii) pyrophosphate, (iii) an enzyme that catalyzes the release of a nucleotide from a nucleic acid hybrid, by pyrophosphorolysis of the 3'-terminus of a strand of the nucleic acid hybrid in the presence of pyrophosphate, and (iv) a suitable nucleotide that can be incorporated in the place of said released nucleotide;

(b) maintaining said reaction mixture for a time period and under conditions that permit (i) pyrophosphorolysis of the 3'-terminus of a strand of a nucleic acid hybrid to produce a released nucleotide and a modified 3'-terminus as well as (ii) the incorporation of said suitable nucleotide into the modified 3'-terminus of the nucleic acid hybrid to produce an incorporated modified 3'-terminus, thereby forming a treated sample; and (c) assaying the treated sample to determine where incorporation of said suitable nucleotide into the hybrid occurred and thereby determining nucleotide sequence of the nucleic acid hybrid.

28. The method of determining a nucleotide sequence of a nucleic acid hybrid according to claim 27 wherein said nucleic acid hybrid is formed by a combination of a nucleic acid probe with a nucleic acid target.

* * * * *

SEQUENCE LISTING

```
<160> NUMBER OF SEQ ID NOS: 45

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 1
```
cggtgcgggc ctcttc                                                16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 2
cggtgcgggc ctctac                                                16

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 3
atagcgaaga ggcccgcacc gatcgcccTt cccaacagtt gcgcagcctg aatggcgaat    60
ggaaa                                                                65

<210> SEQ ID NO 4
<211> LENGTH: 65
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 4
atagcgtaga ggcccgcacc gatcgcccTt cccaacagtt gcgcagcctg aatggcgaat    60
ggaaa                                                                65

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 5
cgatcggtgc gggcctcttc                                            20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 6
atcggtgcgg gcctctac                                              18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic -continued Nucleic Acid Sequences

<400> SEQUENCE: 7
cgatcggtca gggcctcttc                                              20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 8
atcggtacgg gcctctac                                                18

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 9
ttcgccattc aggcagcgca actg                                         24

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 10
acgcaaactt tatca                                                   15

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 11
taaggacgca aactttatca                                              20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 12
acagctaagg acgcaaactt tatca                                        25

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:Synthetic
      Nucleic Acid Sequences

```
<400> SEQUENCE: 13
tagaaatacc acagctaagg acgcaaactt tatca                           35

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 14
aacttaccag tagaaatacc acagctaagg acgcaaactt tatca                45

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 15
gtagtaattg aacttaccag tagaaatacc acagctaagg acgcaaactt tatca      55

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 16
acaccaaaat gtagtaattg aacttaccag tagaaatacc acagctaagg acgcaaactt  60
tatca                                                             65

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 17
aggctcccct tgataaagtt tgcgtcctta gctgtggtat ttctactggt aagttcaatt  60
actacatttt ggtgtggatg                                             80

<210> SEQ ID NO 18
<211> LENGTH: 22
<212> TYPE: DNA
<213> ORGANISM: Homo sapiens

<400> SEQUENCE: 18
acccacagaa aatgatgccc ag                                          22

<210> SEQ ID NO 19
<211> LENGTH: 50
<212> TYPE: DNA
<213> ORGANISM: Homo sapiens

<400> SEQUENCE: 19
```
ttaagtgcaa aaagaacaag tagcttgtat tctatagtgt cacctaaatc          50

<210> SEQ ID NO 20
<211> LENGTH: 29
<212> TYPE: DNA
<213> ORGANISM: Homo sapiens

<400> SEQUENCE: 20
cttgaaggac aaaatacctg tattcctcg                                  29

<210> SEQ ID NO 21
<211> LENGTH: 29
<212> TYPE: DNA
<213> ORGANISM: Homo sapiens

<400> SEQUENCE: 21
cttgaaggac aaaatacctg tattccttg                                  29

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 22
atagcgaaga ggcccgcacc gatcgcc                                    27

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 23
atagcgaaga ggcccgcacc g                                          21

<210> SEQ ID NO 24
<211> LENGTH: 18
<212> TYPE: DNA
<213> ORGANISM: Homo sapiens

<400> SEQUENCE: 24
caccctccag cccccaac                                              18

<210> SEQ ID NO 25
<211> LENGTH: 18
<212> TYPE: DNA
<213> ORGANISM: Homo sapiens

<400> SEQUENCE: 25
caccctccag cccccacc                                              18

<210> SEQ ID NO 26
<211> LENGTH: 16
<212> TYPE: DNA
<213> ORGANISM: Homo sapiens

<400> SEQUENCE: 26
ccctccagcc cccagc                                                16

```
<210> SEQ ID NO 27
<211> LENGTH: 24
<212> TYPE: DNA
<213> ORGANISM: Homo sapiens

<400> SEQUENCE: 27
tctctcctca cctgcagcat caac                                              24

<210> SEQ ID NO 28
<211> LENGTH: 26
<212> TYPE: DNA
<213> ORGANISM: Homo sapiens

<400> SEQUENCE: 28
aggagttggg ggctggaggg tgggaa                                            26

<210> SEQ ID NO 29
<211> LENGTH: 26
<212> TYPE: DNA
<213> ORGANISM: Homo sapiens

<400> SEQUENCE: 29
aggaggtggg ggctggaggg tgggaa                                            26

<210> SEQ ID NO 30
<211> LENGTH: 26
<212> TYPE: DNA
<213> ORGANISM: Homo sapiens

<400> SEQUENCE: 30
aggagctggg ggctggaggg tgggaa                                            26

<210> SEQ ID NO 31
<211> LENGTH: 33
<212> TYPE: DNA
<213> ORGANISM: Homo sapiens

<400> SEQUENCE: 31
gtaacagttg atgctgcagg tgaggagaga gaa                                    33

<210> SEQ ID NO 32
<211> LENGTH: 36
<212> TYPE: DNA
<213> ORGANISM: Homo sapiens

<400> SEQUENCE: 32
tcctccggat caatccccag attcagcagc gactgc                                 36

<210> SEQ ID NO 33
<211> LENGTH: 38
<212> TYPE: DNA
<213> ORGANISM: Homo sapiens

<400> SEQUENCE: 33
actcctccgg atcaatcccc agattcagca gcgactgt                               38

<210> SEQ ID NO 34
<211> LENGTH: 47
<212> TYPE: DNA
<213> ORGANISM: Homo sapiens

<400> SEQUENCE: 34
acctgcagtc gctgctgaat ctggggaatg atcgggagga gtcctgc                     47
```

<210> SEQ ID NO 35
<211> LENGTH: 47
<212> TYPE: DNA
<213> ORGANISM: Homo sapiens

<400> SEQUENCE: 35
acctacagtc gctgctgaat ctggggaatg atcgggagga gtcctgc           47

<210> SEQ ID NO 36
<211> LENGTH: 43
<212> TYPE: DNA
<213> ORGANISM: Homo sapiens

<400> SEQUENCE: 36
gcccttggtc aatcccacga tcgccgaggt gctgcgcctg cgg               43

<210> SEQ ID NO 37
<211> LENGTH: 43
<212> TYPE: DNA
<213> ORGANISM: Homo sapiens

<400> SEQUENCE: 37
gcccttggtc aatcccacga tcgccgaggt gctgcgcctg tgg               43

<210> SEQ ID NO 38
<211> LENGTH: 50
<212> TYPE: DNA
<213> ORGANISM: Homo sapiens

<400> SEQUENCE: 38
aacgggccgc aggcgcagca cctcggcgat ggtggcattg agcaagggca        50

<210> SEQ ID NO 39
<211> LENGTH: 50
<212> TYPE: DNA
<213> ORGANISM: Homo sapiens

<400> SEQUENCE: 39
aacgggccac aggcgcagca cctcggcgat ggtggcattg agcaagggca        50

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 40
cctcttcgct attacttcgc catttgacgt tggag                        35

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 41
gagttctcca acgtcaaatg gcgaacatta                              30

<210> SEQ ID NO 42
<211> LENGTH: 30

```
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 42
gagttcgcca acgtcaaatg gcgaacatta                                         30

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 43
gcatcgatcc aagcagacat gca                                                23

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 44
ggacacttac ca                                                            12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence:Synthetic
      Nucleic Acid Sequences

<400> SEQUENCE: 45
ggacccttac ca                                                            12
```